(12) United States Patent
Levin et al.

(10) Patent No.: US 6,456,863 B1
(45) Date of Patent: *Sep. 24, 2002

(54) MOLDED CATHETER DISTAL END ASSEMBLY AND PROCESS FOR THE MANUFACTURE THEREOF

(75) Inventors: Steven E. Levin, Mountain View; Russell B. Thompson, Los Altos; Sidney D. Fleischman, Menlo Park, all of CA (US)

(73) Assignee: EP Technologies, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/543,250

(22) Filed: Apr. 5, 2000

Related U.S. Application Data

(63) Continuation of application No. 08/943,380, filed on Oct. 1, 1997, now Pat. No. 6,078,830.

(51) Int. Cl.⁷ .................................................. A61B 5/04
(52) U.S. Cl. ........................................... 600/374; 606/41
(58) Field of Search ................................ 600/372, 374; 606/41, 42, 45–50, 27–34; 607/101, 102, 115, 116

(56) References Cited

U.S. PATENT DOCUMENTS

| | | | | |
|---|---|---|---|---|
| 4,559,951 A | * | 12/1985 | Dahl et al. | 600/374 |
| 4,665,604 A | * | 5/1987 | Dubowik | 29/415 |
| 5,409,487 A | | 4/1995 | Jalbert et al. | |
| 5,417,208 A | * | 5/1995 | Winkler | 600/374 |
| 5,617,854 A | | 4/1997 | Munsif | |
| 5,642,736 A | | 7/1997 | Avitall | |
| 5,676,662 A | | 10/1997 | Fleischhacker et al. | |
| 5,685,878 A | | 11/1997 | Falwell | |
| 5,741,249 A | | 4/1998 | Moss et al. | |
| 5,782,760 A | * | 7/1998 | Schaer | 600/381 |
| 5,810,802 A | * | 9/1998 | Panescu et al. | 606/31 |
| 5,855,552 A | * | 1/1999 | Houser et al. | 600/374 |

* cited by examiner

*Primary Examiner*—Michael Peffley
(74) *Attorney, Agent, or Firm*—Lyon & Lyon LLP

(57) ABSTRACT

The present invention includes a catheter having a molded distal end assembly that includes at least one component molded therewithin. In a preferred embodiment, the catheter end assembly includes a plurality of electrodes and lead wires that are all molded into the walls of the assembly. Each such electrode has at least one thermocouple associated with it, and the thermocouple is also molded into the walls of the assembly. In manufacturing the multi-electrode end assembly, lead wires from the coils and thermocouples are preferably spiral wound within the molded walls of the assembly to reduce the possibility that lead wires may become disconnected during manufacturing and use of the catheter. Particular core pin designs with mold blocking techniques are utilized to mold the coils and lead wires into the wall of the end assembly. The molding method is generally applicable to the manufacturing of a variety of catheter distal end components and assemblies.

18 Claims, 14 Drawing Sheets

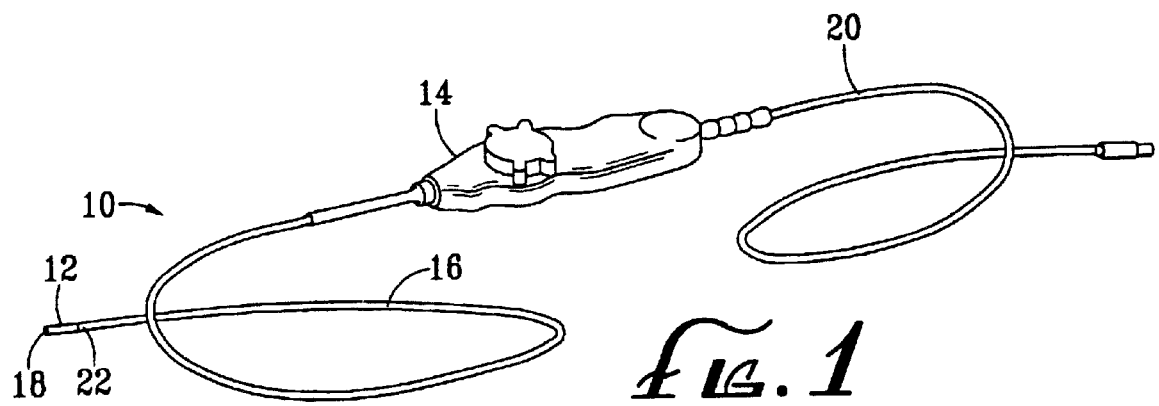
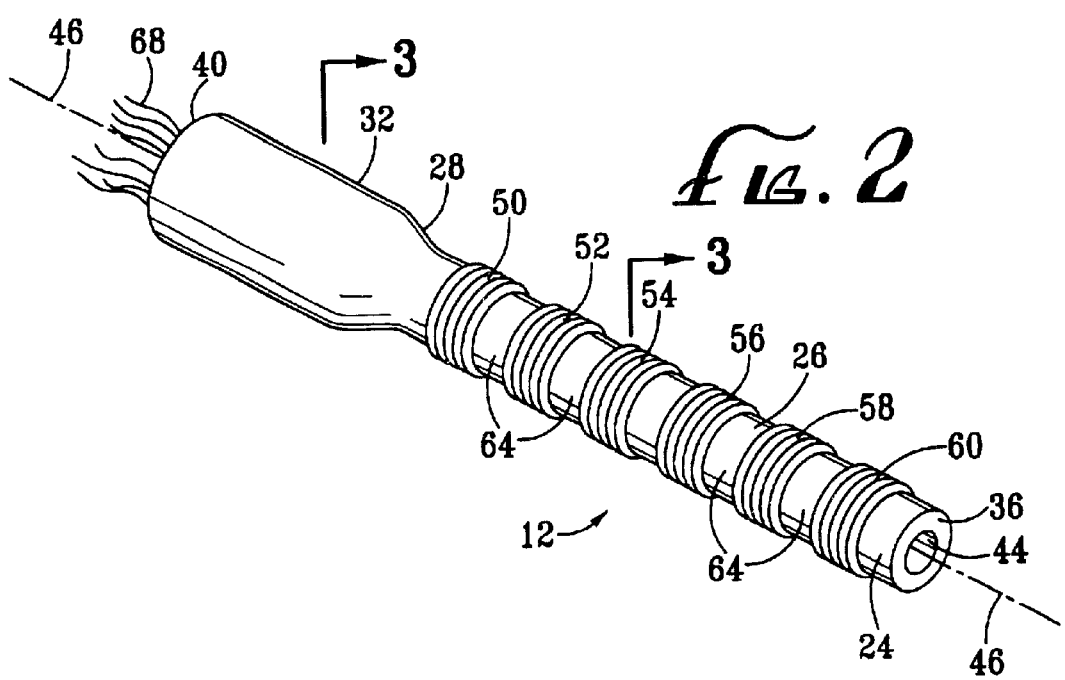

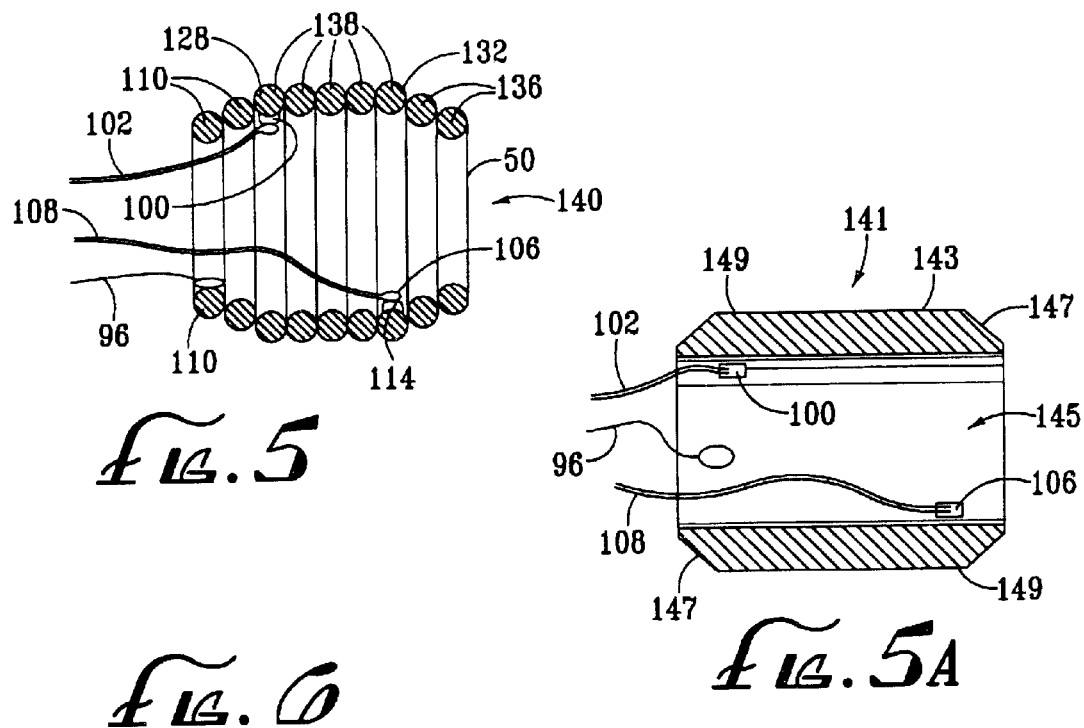
*fig.5*
*fig.5A*
*fig.6*
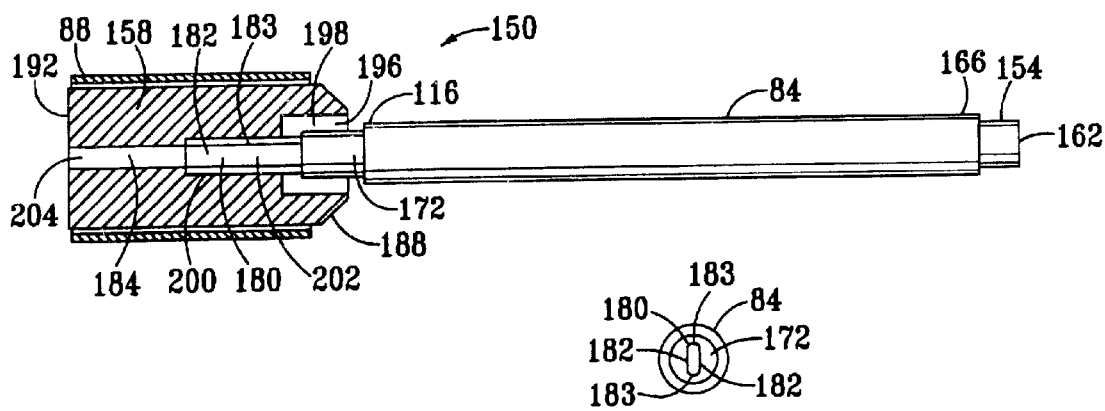
*fig.7*
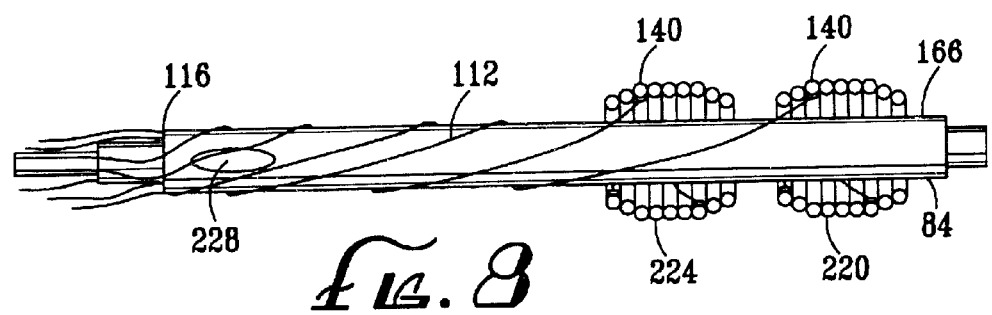
*fig.8*

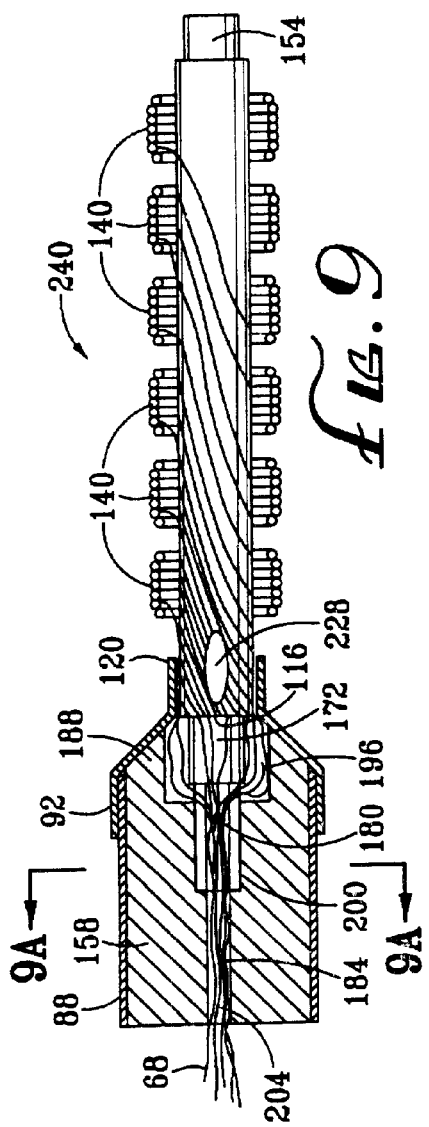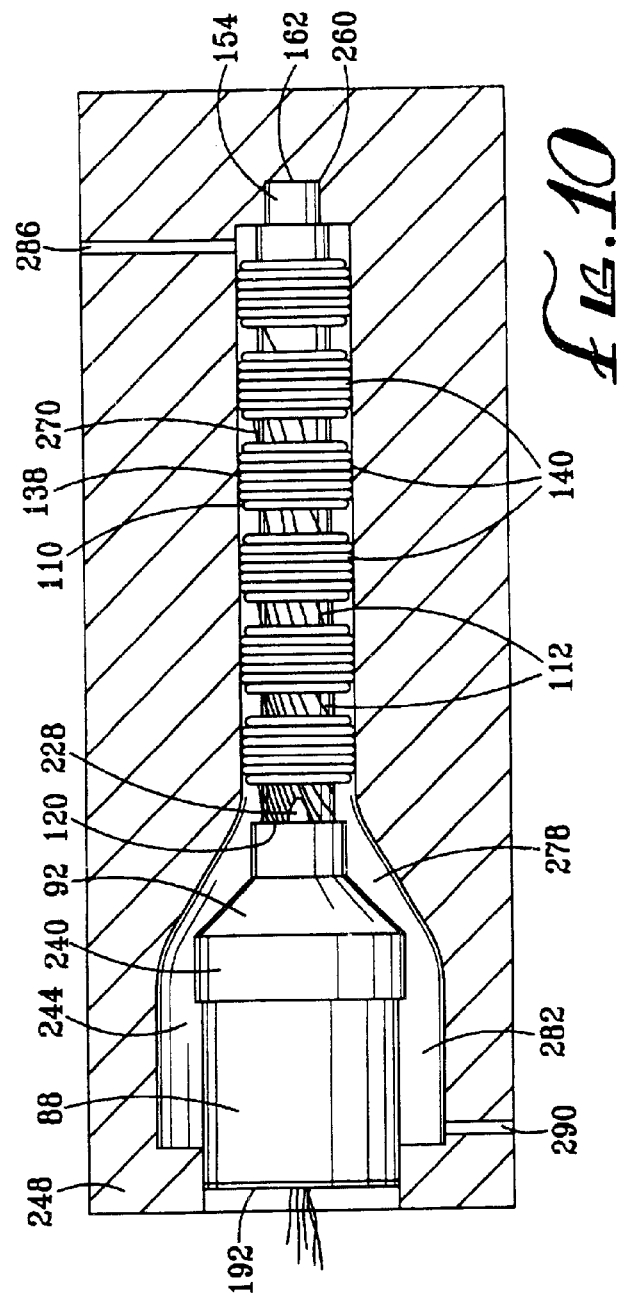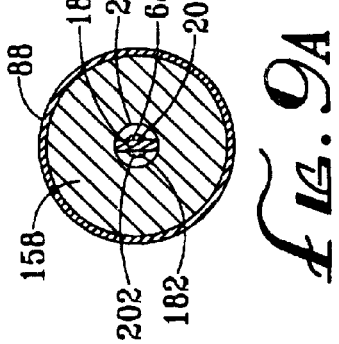

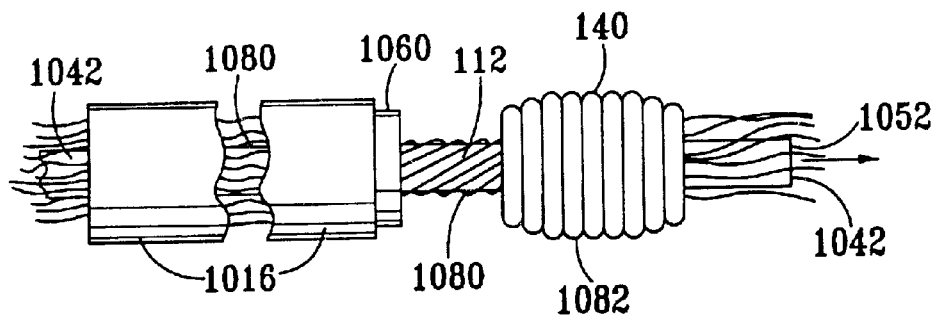
*Fig.* 20
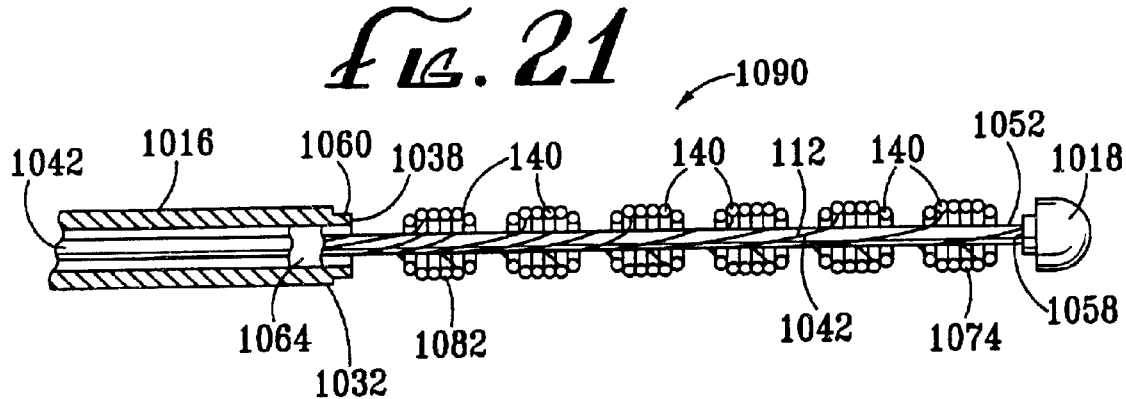
*Fig.* 21
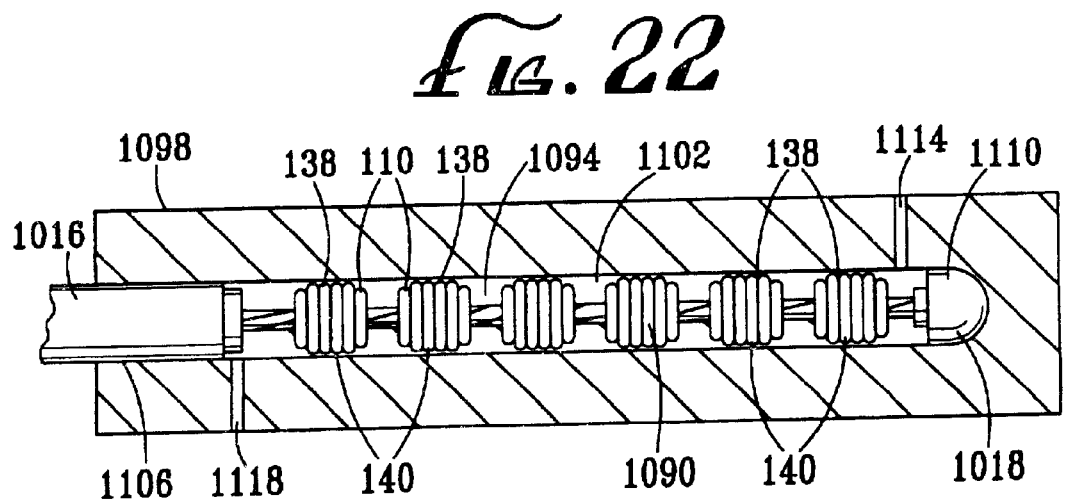
*Fig.* 22

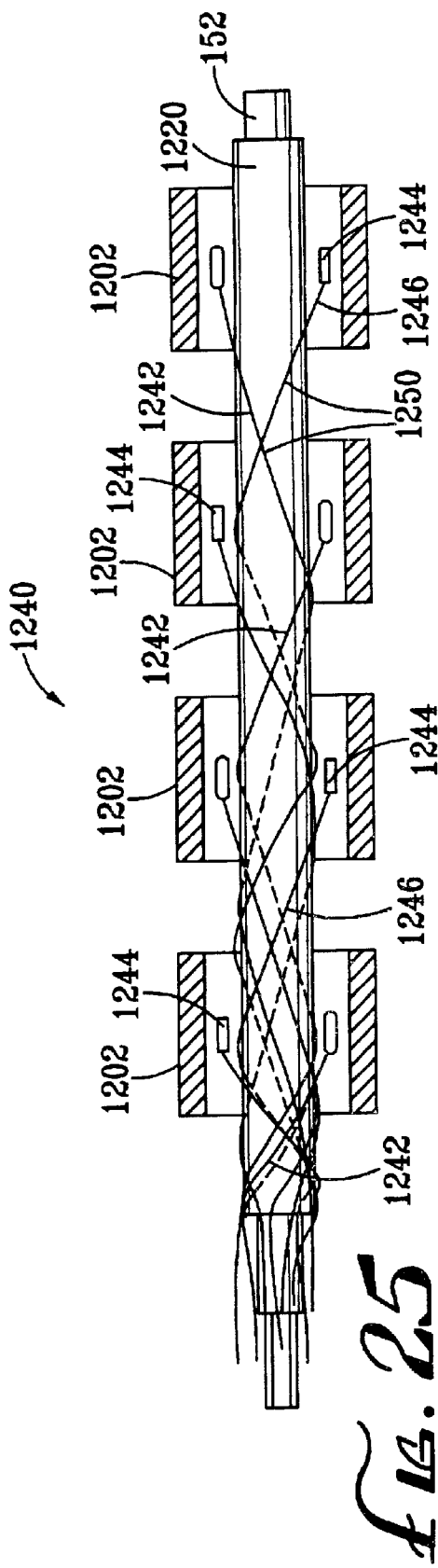
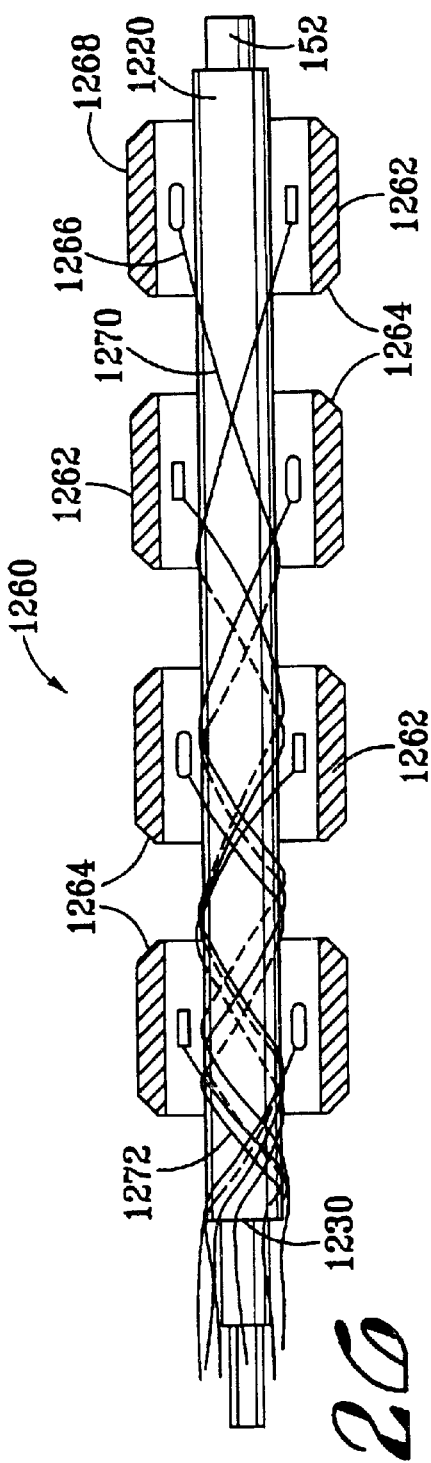

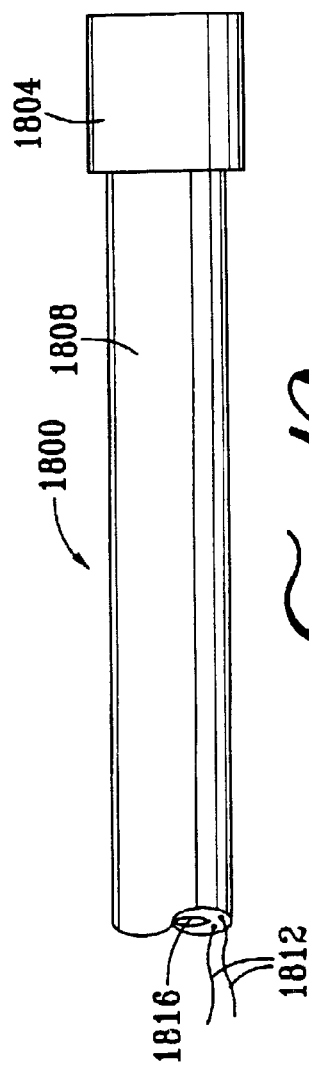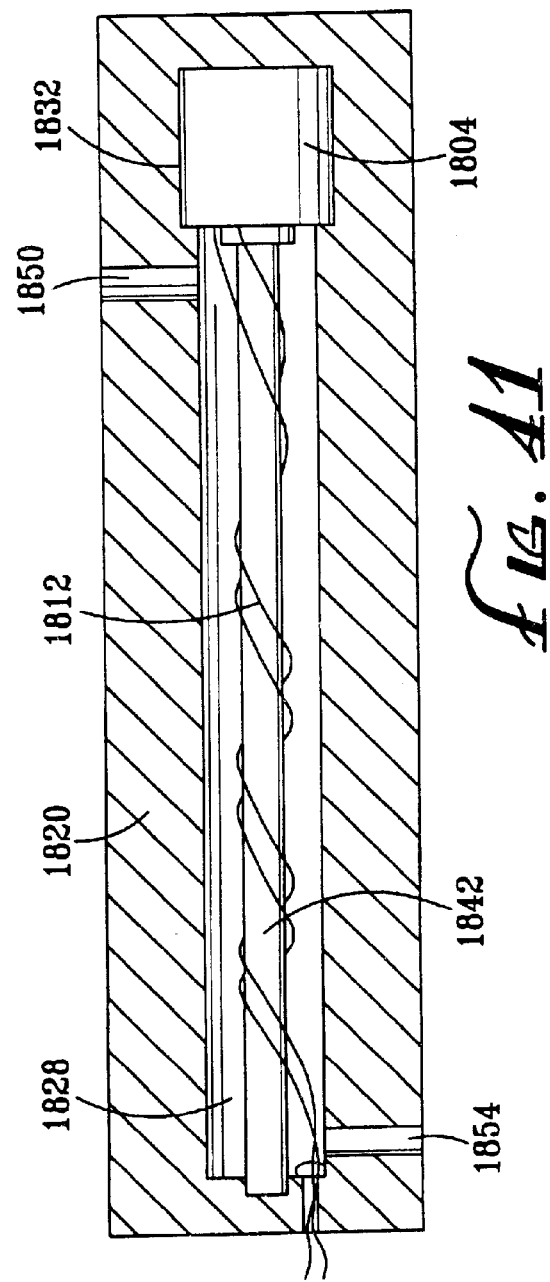

MOLDED CATHETER DISTAL END ASSEMBLY AND PROCESS FOR THE MANUFACTURE THEREOF

This is a continuation of application Ser. No. 08/943,380, filed on Oct. 1, 1997 now U.S. Pat. No. 6,078,830.

BACKGROUND OF THE INVENTION

1. Field of the Invention

The present invention relates generally to catheters and more particularly to molded catheter distal ends, including molded multi-electrode distal ends, and other molded catheter distal end components and methods for the manufacture thereof.

2. Description of the Prior Art

Catheter distal end assemblies are currently manufactured in a tedious process that involves many steps and takes considerable time. Briefly, with regard to a multi-electrode catheter distal end assembly, a section of extruded polymer tube (the distal tube) is selected and the proximal end of the distal tube is expanded for joinder to the main body tube of a catheter. The polymer tube is then pierced in several places and a plurality of coil lead wires and thermocouple lead wires are threaded through the pierced holes. Anticipated locations on the distal tube for the plurality of coils are identified and one or more thermocouples are placed so as to be positioned under each coil. The thermocouples are then bonded to the distal tube in the specified locations. Thereafter, each coil is sequentially slid down the distal tube over the plurality of in-place thermocouples in a time consuming, precise process to avoid disturbing the thermocouples and lead wires as the coils are slid over them. The lead wires are particularly thin and fragile, and the inadvertent disconnection of even one lead wire results in an inoperative device. When properly positioned, the coil ends of each coil are covered with adhesive to bond them in place. Thereafter, a steering assembly is inserted through the distal tube and a tip electrode is soldered to the distal end of the steering assembly, and an electrical lead is attached to the tip electrode. The proximal end of the distal tube is then joined to the main catheter body.

SUMMARY OF THE INVENTION

The present invention includes a catheter having a molded distal end assembly that includes at least one component. In a preferred embodiment, the catheter end component includes one or more electrodes that are molded into the walls of the assembly. In an ablation type electrode assembly, one or more temperature sensors may be associated with an electrode. In manufacturing this multi-electrode end assembly, lead wires from the coils and temperature sensors are preferably spiral wound and molded into the walls of the assembly to reduce the possibility that the lead wires may become disconnected during manufacturing or later during use of the catheter, and also to increase the flexibility of the distal end assembly. Particular core pin designs with mold blocking techniques are utilized to mold the coils and lead wires into the wall of the end assembly. Specific embodiments of the molding method include separate distal end assemblies, integrally molded distal end assemblies and molded components of catheter end assemblies.

It is an advantage of the molded distal end assembly of the present invention that it has a smooth outer surface.

It is an advantage of some of the molded multi-electrode distal end assemblies of the present invention that they have a smooth surface at the edges of the electrodes and between the electrodes.

It is a further advantage of the molded multi-electrode distal end assembly of the present invention that it has a unitary outer surface that eliminates the possibility for blood ingress into the catheter lumen.

It is yet another advantage of the molded multi-electrode distal end assembly of the present invention that the electrode leads are molded in place, to reduce the possibility of disconnection during device usage.

It is yet a further advantage of the molded multi-electrode distal end assembly of the present invention that electrodes can be more accurately and closely spaced along the assembly body.

It is still another advantage of the molded multi-electrode distal end assembly of the present invention that the temperature sensors are bonded to the electrodes, thus providing a reliable feedback reading.

It is an advantage of the unitary, molded catheter assembly which includes a molded multi-electrode distal end assembly of the present invention that the molding of the multi-electrode assembly to the main catheter body tubing eliminates a difficult-to-make joint.

It is another advantage of the unitary, molded multi-electrode catheter assembly of the present invention that the main catheter body, the steering assembly, the tip electrode and the multi-electrode assembly are all molded together to form a single bonded unit.

It is an advantage of the manufacturing method for the molded distal end assembly of the present invention that it is easier, faster and less expensive than the prior art methods by eliminating many manual steps.

It is an advantage of the manufacturing method for the unitary, molded catheter assembly of the present invention that in one molding step, the steering assembly and tip electrode are joined with the multi-electrode assembly.

These and other features and advantages of the present invention will become understood by those skilled in the art upon reading the following detailed description and claims.

IN THE DRAWINGS

FIG. 1 is a perspective view of a catheter that includes a molded multi-electrode catheter end assembly of the present invention;

FIG. 2 is a perspective view of a molded multi-electrode catheter end assembly of the present invention;

FIG. 5 is a side cross-sectional view depicting a coil-thermocouple assembly, as utilized in the present invention;

FIG. 5A is a side cross-sectional view depicting an alternative ring-thermocouple assembly, utilizable in the present invention;

FIG. 6 is a side cross-sectional view depicting a two part core end assembly utilized in the manufacturing of the present invention depicted in FIG. 2;

FIG. 7 is an end elevational view of the distal core pin depicted in FIG. 6;

FIG. 8 is a side elevational view depicting a first assembly step in the manufacturing of the present invention depicted in FIG. 2;

FIG. 9 is a side cross-sectional view depicting a further manufacturing step of the present invention depicted in FIG. 2;

FIG. 9A is a cross-sectional view of the assembly depicted in FIG. 9, taken along lines 9A—9A of FIG. 9;

FIG. 10 is a side cross-sectional view depicting an assembled stage of the device depicted in FIG. 2 disposed within a mold cavity;

FIG. 20 depicts a further assembly step in the manufacturing of the device depicted in FIGS. 16 and 17;

FIG. 21 depicts a third assembly step in the manufacturing of the device depicted in FIGS. 16 and 17;

FIG. 22 depicts the assemblage resulting from the third assembly step depicted in FIG. 21 disposed within a mold for manufacturing;

FIG. 25 is a side cross-sectional view depicting the four ring electrodes of FIG. 23 disposed upon a distal core pin assembly;

FIG. 26 is a side cross-sectional view depicting an alternative four ring electrode assembly mounted upon a distal core pin assembly;

Figure 32:
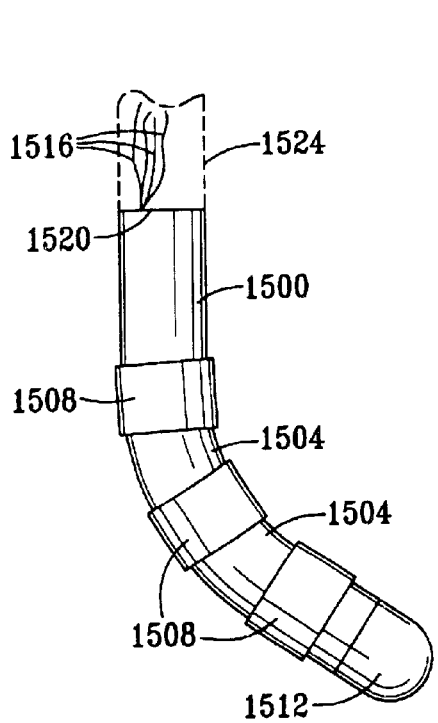
FIG. 32 is a side elevational view of a curved catheter distal end assembly of the present invention.
Figure 33:
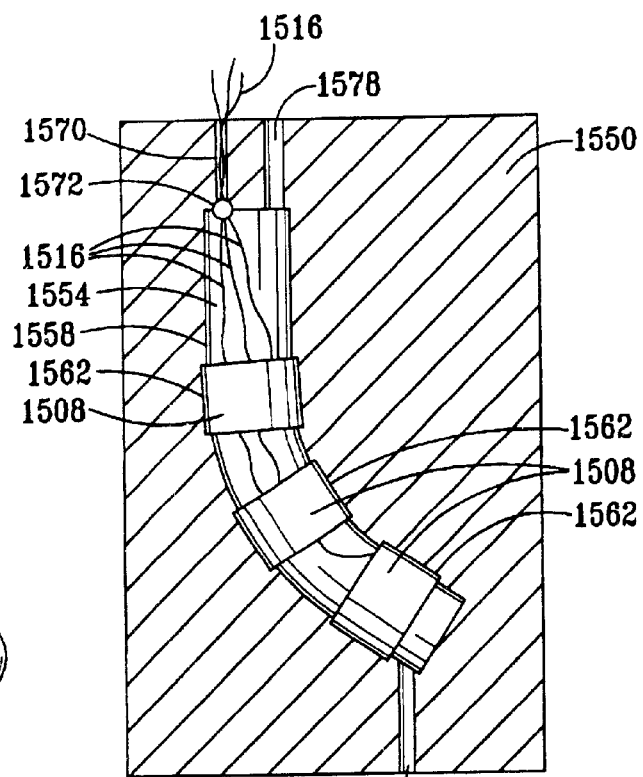
Figure 34:
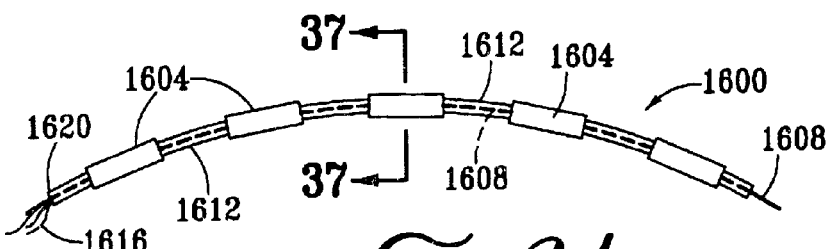
Figure 36:
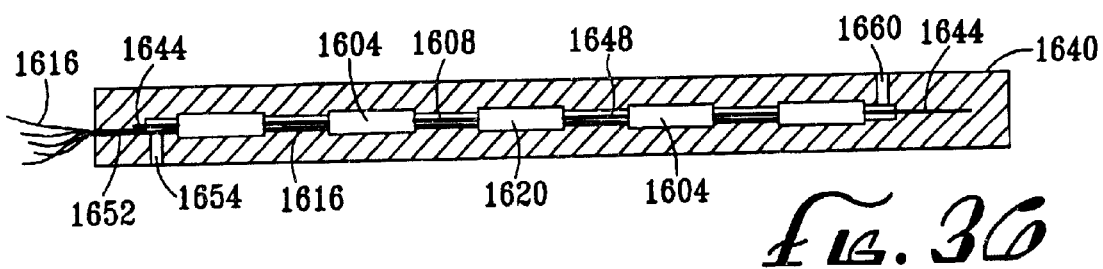
Figure 35:
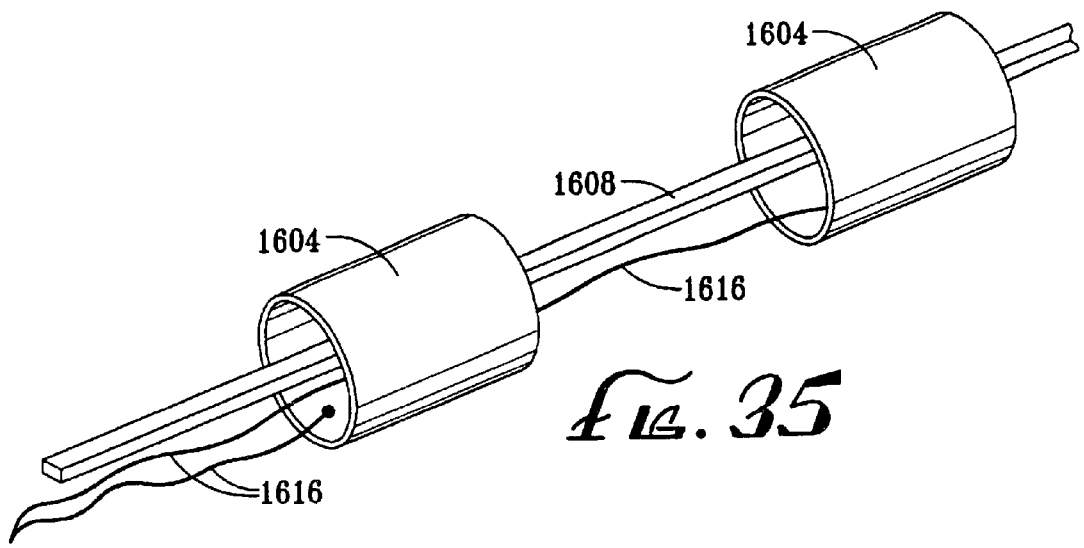
Figure 37:
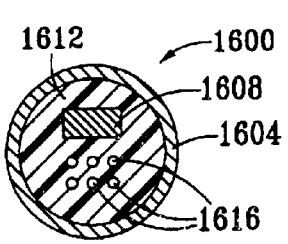
Figure 38:
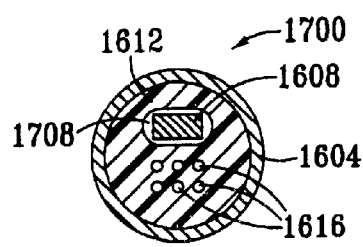
Figure 39:
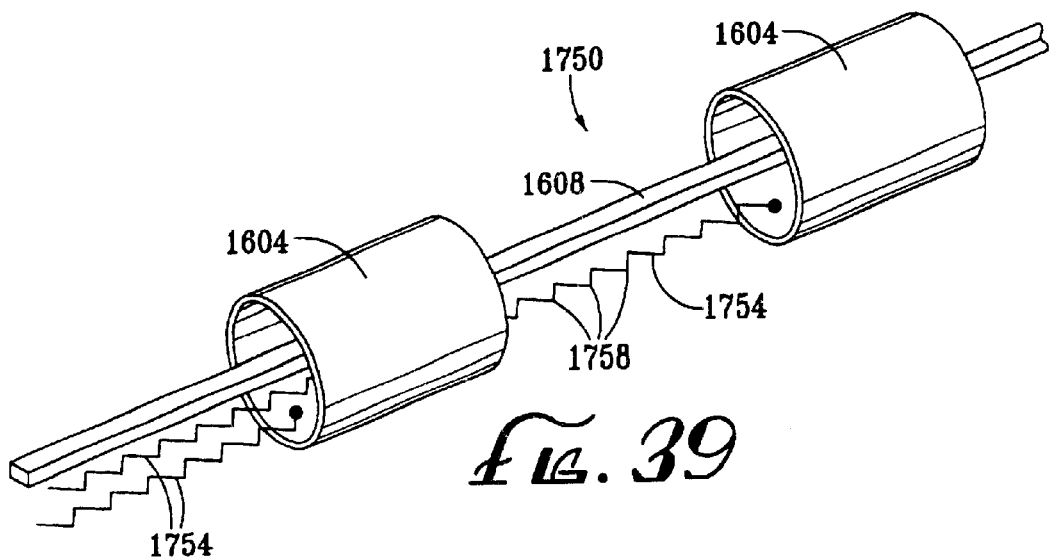

FIG. 33. depicts a ring assemblage disposed within a mold for manufacturing the embodiment depicted in FIG. 32;

FIG. 34 is an elevational view of a basket spline catheter component of the present invention;

FIG. 35 is an enlarged perspective view of a portion of the device depicted in FIG. 34;

FIG. 36 depicts the assemblage of FIG. 36 disposed within a mold for manufacturing the device depicted in FIG. 34;

FIG. 37 is a cross-sectional view of the device depicted in FIG. 34, taken along lines 37—37 thereof;

FIG. 38 is a cross-sectional view similar to FIG. 37, depicting an alternative embodiment to the device depicted in FIG. 37;

FIG. 39 is a perspective view similar to FIG. 35, depicting an alternative embodiment to the embodiment depicted in FIG. 35;

FIG. 40 depicts a molded imaging distal end assembly of the present invention; and FIG. 41 depicts an assembly for manufacturing the imaging distal end assembly of FIG. 40, disposed within a mold block.

DETAILED DESCRIPTION OF THE PREFERRED EMBODIMENT

Referring to FIG. 1 a catheter device 10 of the present invention includes the molded catheter distal end assembly 12 of the present invention. As shown therein, the catheter 10 generally includes a handle 14, a guide tube 16, the molded distal end assembly 12, a tip 18 and an interconnection cable 20 that is engagable with a connector (not shown) that is disposed in the proximal end of the handle 14. The molded distal end assembly 12 is bonded to the distal end of the guide tube 16 at a joint 22. While the catheter 10 can be used in many different environments, this specification will generally describe its use to provide electrophysiologic therapy in the interior regions of the heart. In this application the molded distal end assembly 12 will include a plurality of electrodes. In use, a physician grips the handle assembly 14 to steer the guide tube assembly 16 through a main vein or artery, such as the femoral artery, into an interior region of the heart that is to be treated. The physician further manipulates the device to place the multi-electrode assembly 12 and tip 18 in contact with the tissue that is to be ablated. The physician then introduces radio frequency energy from a source (not shown) through the cable 20, through electrical leads in the guide tube assembly 16 to the multi-electrode assembly 12 to ablate the heart tissue located proximate the multi-electrode assembly 12.

As depicted in FIG. 2, the multi-electrode assembly 12 is a generally cylindrical member having molded tubular wall 24 that includes a reduced diameter distal wall section 26, a flared wall section 28 and an enlarged diameter proximal wall section 32. It is to be noted that FIG. 2 as well as other drawings herein is not drawn to scale, but rather, certain components are enlarged to better depict and describe the many features of the present invention. The distal wall section 26 terminates in a distal end face 36 and the proximal wall section 32 terminates in a proximal end face 40. The wall 24 generally defines a central lumen 44 which has a central longitudinal axis 46. When the catheter 10 is assembled, a catheter steering mechanism (not shown) is positioned within the lumen 44 and the tip electrode 18 is engaged to the distal end of the steerer mechanism. The multi-electrode assembly 12 includes a plurality of RF electrodes disposed within the distal wall section 26. Six coil electrodes (50, 52, 54, 56, 58 and 60) are depicted in FIG. 2, it being understood that a greater or lesser number of electrodes may be incorporated into various embodiments of the assembly 12, and that ring type electrodes and other electrode configurations are utilizable in place of coil electrodes. An axial space 64 is formed between each of the electrodes 50–60 to maintain the electrical isolation. The proximal end 40 of the multi-electrode assembly 12 is engagable with a distal end of the catheter guide tube 16 at the bonded joint 22 (shown in FIG. 1). A plurality of wire leads 68 project axially rearwardly through the proximal end 40 and through the guide tube 16 to a pin connector (not shown) disposed in the handle 14 for interconnection with the electrical cable 20. The wire leads 68 are interconnected to the electrodes and to a plurality of temperature sensors within the distal wall section 26, as is next discussed.

Figure 3:
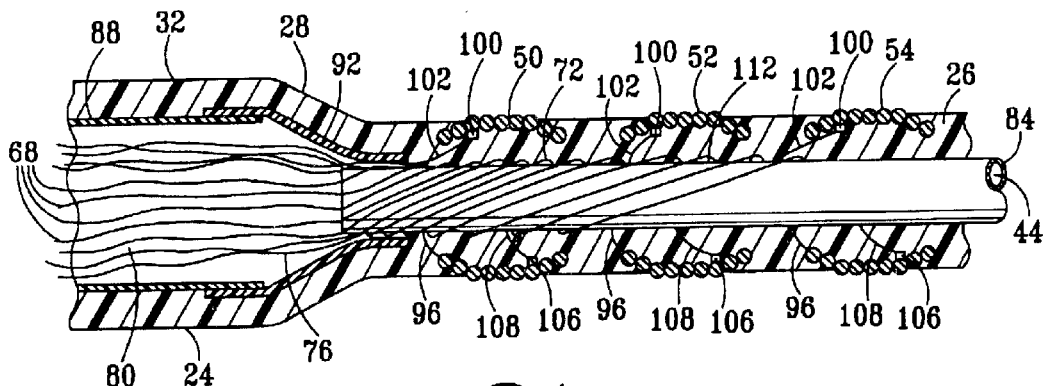
FIG. 3 is a side cross-sectional view of the molded, multi-electrode catheter end assembly depicted in FIG. 2, taken along lines 3—3 of FIG. 2.

FIG. 3 is a side cross-sectional view of a section 3—3 of the multi-electrode assembly 12 depicted in FIG. 2, showing only electrodes 50, 52 and 54, it being understood that the electrical and molding engagement features of electrodes 56, 58 and 60 are substantially identical to that of electrodes 50, 52 and 54. The central lumen 44 includes a distal lumen section 72 defined by the distal wall section 26 and having a generally reduced diameter, a flared lumen section 76 defined by the flared wall section 28, and a proximal lumen section 80 defined by the proximal wall section 32 and having a generally enlarged diameter. The inner sidewall of the distal lumen section 72 is formed by a thin wall tubular section 84. The tubular section 84 may be comprised of a high temperature thermoset polymer such as polyimide, a section of shrink tubing or other suitable thin wall cylindrical members. In a like manner, the inner sidewall of the proximal lumen section 80 is formed by a thin wall tubular section 88, that may be comprised of a high temperature thermoset polymer such as a polyimide, a section of shrink tubing or other suitable thin wall cylindrical members. The inner sidewall of the flared lumen section 76 is similarly formed by a flared tubular section 92, preferably composed of shrink tubing.

Figure 4:
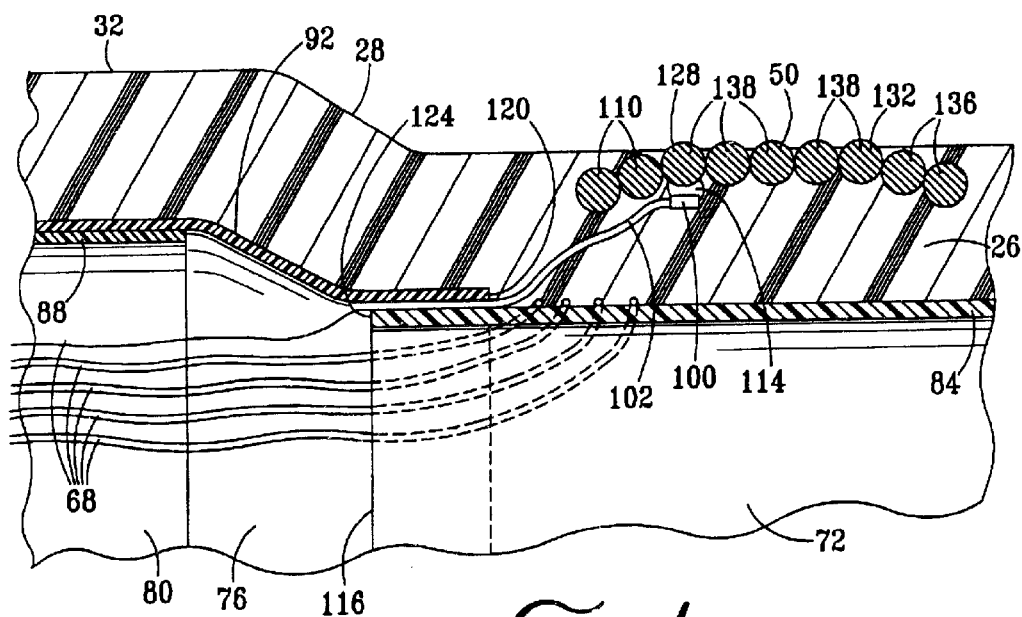
FIG. 4 is an expanded side cross-sectional view showing details of the device as depicted in FIG. 3.

Referring also to FIGS. 4 and 5, each electrode 50, 52, 54 has an electrically isolated RF power lead wire 96 engaged to it. A first temperature sensor 100 having a bifilar electrical lead wire 102 engaged thereto is disposed near the proximal end of each electrode 50, 52, 54 to provide feedback information to the operator. As shown in FIG. 4, the temperature sensor 100 of electrode 50 is bonded to winding 128 of electrode 50 utilizing a thermally conductive and electrically non-conductive adhesive 114. A second temperature sensor 106 having a bifilar electrical lead wire 108 engaged thereto may also be disposed near the distal end of each electrode 50, 52 and 54 to provide further feedback information to the operator. Each temperature sensor 100 and 106 is bonded to its respective electrode location utilizing a thermally conductive but electrically non-conductive adhesive 114.

Catheter distal end assemblies that are designed for different purposes, such as sensing, pacing or ablation, utilize electrodes having differing shapes and characteristics. In a preferred embodiment of an ablation catheter distal end assembly, the proximal and distal end portions of each electrode (such as electrode 50) are preferably molded into the body of the distal wall section 26. As depicted in FIGS. 4 and 5, the individual proximal windings 110 and distal windings 136 of a coil electrode 50 are depicted in a preferred molded-in disposition within the molded distal wall section 26. To achieve the molded-in effect, the outer diameter of coil windings 110 and 136 is manufactured to be less than the outer diameter of coil windings 128 and 132 and the remaining mid-coil windings 138, such as is depicted in FIG. 5. The decrease in the outer diameter of the individual coil windings can be achieved by tapering the coil, such that the outer diameter of the individual coil windings is changed. The decreased diameter may also be achieved by grinding the outer surface of coil windings 110 and 136 to make the coil wire thinner at the proximal and distal ends. The coil end windings 110 and 136 are preferably molded into the distal wall section 26 because the tissue adjacent the end windings receives a higher electrical power density than tissue adjacent the middle windings 138 of the coil electrode. The higher electrical power density can lead to uneven effects upon the tissue disposed proximate the coil electrode, and molding the end windings of the coil electrodes into the sidewall produces a more even electrical power density at the outer surface of the assembly 12 that is in contact with the tissue. In the preferred embodiment, the temperature sensor 100 is preferably engaged to a portion of the electrode 50 that is in contact with the tissue, and as close to the end of the electrode as is feasible; thus, the engagement of a temperature sensors 100 and 106 to exposed coil windings 128 and 132 respectively is preferred.

A ring electrode 141 that is suitable for use in the present invention is depicted in FIG. 5A. The electrode 141 is a cylindrical member having sidewalls 143 which define a central bore 145. Where the electrode is utilized for ablation purposes, the outer edges 147 of the sidewalls 143 are removed, such that the molded-in effect can be achieved. As with the coil electrode depicted in FIG. 5, an electrode lead wire 96 is engaged to the sidewalls 143 and two thermocouples 100 and 106, having associated bifilar lead wires 102 and 108 respectively, are engaged proximate the end portions 149 of the sidewall 143 where the electrode will make contact with bodily tissue. The utilization of ring electrodes 141 is depicted and described in detail herebelow.

As is described in greater detail herebelow, the electrical lead wires 96 that are connected to each of the electrodes 50–60 and the temperature sensors lead wires 102 and 108 are molded into the distal wall section 26. during the manufacturing process. In the preferred embodiment, each of the electrode lead wires 96 and the temperature sensor lead wires 102 and 108 are preferably wound in a spiral manner 112 around the distal lumen tubing 84 within the molded distal wall section. 26, in order to help prevent the disconnection of the lead wires from their respective electrodes and temperature sensors during manufacturing and when the device 12 is laterally distorted by the steering assembly as the catheter is utilized. The inventors have found that some lead wire disconnection may occur during manufacturing and during lateral distortion, when the electrode and temperature sensor lead wires are merely axially drawn back within the molded distal wall section 26 rather than being drawn back in the spiral manner 112. Additionally, an electrode end assembly with spiral wound lead wires 112 is more flexible than a similar assembly having axially drawn back lead wires. With regard to FIG. 3, for ease of depiction and comprehension, the depiction. of lead wires from electrodes 56, 58 and 60, and their associated temperature sensors have been omitted; it being understood that an operational device having six electrodes (as depicted in FIG. 2), would have lead wires from all of the electrodes and their associated temperature sensors disposed in a spiral manner 112 around the distal tube section 84. All such lead wires would project rearwardly through the proximal end 40 and through the guide tube 16 to the pin connector (not shown) in the handle 14.

As discussed above and depicted in FIG. 3, each of the electrode and temperature sensor lead wires are fixedly engaged within the molded distal wall section 26; whereas, the lead wires within the proximal lumen section 80 are freely disposed. As is best seen with the aid of FIG. 4, the lead wires emerge from the molded distal wall section 26 into the flared lumen section 76 through the flared wall section 28. For example, the bifilar temperature sensor lead wire 102 is engaged to the temperature sensor 100 and fixedly molded within the distal wall section 26 and drawn rearwardly towards the proximal end 116 of the distal tubular member 84 which defines the distal lumen section 72. The lead wire 102 passes between the distal end 120 of the flared section tubular member 92 and the proximal end 116 of the distal tubular section 84, such that the lead wire 102 becomes freely disposed within the flared lumen at the junction edge point 124 between the proximal end 116 of the distal tubular section 84 and the flared tube portion 92. As is further depicted in FIG. 4, each of the electrode and temperature sensor lead wires are released from their molded engagement within the distal wall section 26 at the junction edge 124.

A preferred method for manufacturing the molded multi-electrode catheter distal end assembly 12 depicted in FIGS. 1–4 is next discussed with the aid of FIGS. 5–11. A first step in the manufacturing of the assembly 12 is the selection or preparation of a plurality of electrodes such as coil electrode 50. While a suitable assembly 12 can be created utilizing electrodes having a uniform outer diameter, as has been discussed hereabove, electrodes of this preferred embodiment are coil electrodes that are formed with tapered ends (see FIG. 5) such that the outer coil windings (110 and 136) have a reduced outer diameter.

Having selected or manufactured a plurality of suitable electrodes (such as coil electrodes 50-60), a coil lead wire 96 is engaged to each coil by soldering, welding or a similar bonding method. The next step in the manufacturing process is to bond two thermocouples 100, with attached bifilar lead wires 102 to each coil, as is depicted in FIG. 5. The two thermocouples 100 and 106 (with attached bifilar lead wires 102 and 108 respectively) are bonded to coil windings 128 and 132 utilizing an electrically non-conductive adhesive 114 which preferably is a good conductor of thermal energy. A preferred adhesive for this purpose is a high temperature epoxy adhesive. The result of these steps is the creation of an electrode-thermocouple assembly 140 depicted in FIG. 5.

A next step in the manufacturing process of the multi-electrode distal end assembly 12 is the preparation of a mold core pin. FIG. 6 depicts a first core pin embodiment 150 having a two part core pin, including a distal core pin 154 and a proximal core pin 158 shown in cross-section. The distal core pin 154 serves to form the distal lumen section 72 in the multi-electrode assembly 12, while the proximal core pin 158 serves to form both the flared lumen section 76 and the proximal lumen section 80 of the multi-electrode assembly 12. The distal tubular section 84 is mounted upon the distal core pin 154 and the proximal tubular section 88 is mounted upon the proximal core pin 158.

The distal core pin 154 includes a distal end portion 162 which projects beyond the distal end 166 of the distal tubular section 84. The proximal end portion 172 of the distal core pin 154 projects beyond the proximal end 116 of the distal tubular section 84. As is further seen with the aid of FIG. 7, an end elevational view of the distal core pin 154, the distal core pin 154 also includes a reduced diameter portion 180 which has flat sides 182 and rounded top and bottom edges 183, and which projects rearwardly from the proximal end 172 of the distal core pin 154.

The proximal core pin 158 is a generally cylindrical member having a stepped bore 184 formed therethrough. The proximal core pin 158 has a larger outer diameter than that of the distal core pin 154 and includes an inwardly tapered distal end 188 and a generally flat proximal end 192. The stepped bore 184 is formed with a distal bore section 196 having a diameter that is larger than the diameter of the distal core pin 154, such that the proximal end 172 of the distal core pin 154 is insertable within the bore 184 with a gap 198 existing therebetween. As is described in detail hereinafter with the aid of FIGS. 9 and 9A, the lead wires from the coil-thermocouple assemblies 140 will pass through gap 198. A second inner bore portion 200 of the bore 184 has a reduced diameter relative to bore section 196 and it is formed for holding the rearwardly projecting blade like portion 180 of the distal core pin 154. The diameter of the bore section 200 is only slightly larger than the diameter of the blade like portion 180 such that the rounded top and bottom edges 183 of the blade like portion 180 are snugly engageable within the bore 200. A gap 202 between the flat sides 182 of the blade like portion 180 and the cylindrical wall surface of the bore 200 is thus formed for the passage of the coil-thermocouple assembly lead wires therethrough. A third proximal portion 204 of the bore 184 is formed between the bore section 200 and the end face 192 of the proximal core pin 158. The bore section 204 has a reduced diameter relative to bore section 200 and provides a passage for the coil-thermocouple lead wires therethrough.

A next step in the manufacturing process of the assembly 12 is the placement of a plurality of coil-thermocouple assemblies 140 (as depicted in FIG. 5) upon the distal tubular section 84, as is depicted in FIG. 8. With reference to FIG. 8, a first coil-thermocouple assembly 220 is positioned at the distal end 166 of the distal tubular section 84. The coil and thermocouple lead wires from the coil-thermocouple assembly 220 are then wound in a spiral manner 112 around the distal tubular member 84. The coil-thermocouple assembly 220 and its lead wires may be temporarily held in place using a small quantity of molding material. Thereafter, a second coil-thermocouple assembly 224 is-mounted upon the distal tubular section 84 by inserting the lead wires of coil-thermocouple assembly 220 through it, and then sliding it from the proximal end 116 of the distal tubular member 84 over the spiral wound lead wires of the first coil-thermocouple assembly 224. When the second coil-thermocouple assembly 224 is in position, the coil and thermocouple lead wires from it are wound in a spiral manner 112 around the distal tubular member 84. The coil-thermocouple assembly 224 and its lead wires may be temporarily held in place using a small quantity of molding material.

Thereafter, the remaining coil-thermocouple assemblies (not shown in FIG. 8) are sequentially mounted in the same manner upon the distal tubular section 84 with the lead wires from the subsequent coil-thermocouple assemblies being wound in a spiral manner 112 around the distal tubular section 84. This process is continued until all of the coil-thermocouple assemblies for the particular multi-electrode assembly 12 are mounted on the distal tubular section 84 with spiral wound lead wires. At this stage, it will be appreciated that a significant number of lead wires are wound around the distal tubular member 84. The inventors have found that it is then helpful to utilize a small quantity of adhesive 228 near the proximal end 116 of the tubular member 84 to hold the lead wires in position during the assembly and subsequent molding steps described hereinafter. When all of the coil-thermocouple assemblies 140 have been mounted upon the distal tubular section 84, a completed distal assembly 240 is created; such an assembly is depicted in FIG. 9.

FIGS. 9 and 9A depict a completed core pin manufacturing assembly 240. As depicted therein, all of the lead wires 68 from the distal assembly 232 have been drawn through the lead wire bore 184 of the proximal core pin 158, and the proximal end portion 172 of the distal core pin 154 is disposed within the distal bore portion 196 of the bore 184. Likewise, the projecting blade like portion 180 of the distal core pin 154 is engaged within the middle bore portion 200 of the proximal core pin 158. The lead wires 68 pass through the gaps 198 and 202 formed between the proximal core pin bore sections 196 and 200 and the corresponding distal core pin portions 172 and sides 182 respectively, as mentioned hereabove with regard to FIG. 6.

A generally tubular section of shrink tubing 92 is next placed over the tapered distal face portion 188 of the proximal core pin 158, such that the distal end 120 of the shrink tubing section 92 projects over the proximal end 116 of the distal tubular section 84. The shrink tubing 92 is next heated to shrink its dimensions to conform to the core pin surfaces as depicted in FIG. 9. The completed core pin manufacturing assembly 240, as depicted in FIG. 9, is then ready for insertion into an injection mold, as is next discussed.

FIG. 10 depicts the core pin manufacturing assembly 240 of FIG. 9 disposed within an injection mold cavity 244 of a mold block 248. As depicted therein, the distal end 162 of the distal core pin 154 projects into a centering recess 260 formed in the mold block 248. The proximal end face 192 of the proximal core pin 158 projects outwardly of the mold block 248. The mold cavity 244 includes a distal portion 270 having a diameter that matches the outer diameters of the coil-thermocouple assemblies 140, such that the outer surfaces of the mid-windings 138 of the coils make contact with the sidewall of the distal portion 270 of the cavity. The end windings 110, 128, 132, 136 of the coils do not contact the surface of the distal portion 270 of the cavity due to the tapering of the coils, such that the end windings will become molded into the molded wall of the multi-electrode assembly after the molding process is complete. The mold cavity 244 also includes a flared cavity portion 278 and a proximal cavity portion 282 that form the flared 28 and proximal 32 walls of the assembly 12. An injection mold inlet passage 286 near the distal cavity end 270, and at least one mold outlet 290 located near the proximal end of the proximal cavity portion 282 are utilized to facilitate the injection molding process.

Having placed the assembly 240 into the mold cavity 244, it will be appreciated that a molding material is injected into the inlet orifice 286 to flow completely through the coil assemblies 140 and around the spiral wound lead wires 74 and rearwardly to form the flared and proximal wall portions and outward through the outlet orifice 290 as an indication that the mold cavity is completely filled. A preferred molding material is Pebax®, a poly ether block amide that is similar to Nylon. Pebax® is a registered trademark of Atochem. Thereafter, the appropriate mold curing steps are undertaken, following which the cured part is removed from the mold and the proximal 158 and distal 154 core pins are removed from the cured part. Following the removal of the core pins, the multi-electrode assembly 12 is completed as depicted in FIG. 2 hereabove. To complete the catheter assembly 10 as is shown in FIG. 1, the steering mechanism is inserted into the central lumen 44 and the tip 18 is engaged to it. The tip is electrically connected to a tip lead wire (not shown) and adhesively bonded to the distal end face 36 of the sidewall 24 and the proximal end face 40 is adhesively bonded at joint 22 to the distal end of the guide tube 16.

The removal of the core pin from the molded distal assembly is an important step of the molding operation. Those skilled in molding technique will understand that various techniques can be used. The core pin can be polished and/or plated to provide a smooth surface finish. It can be coated with a mold release compound, such as Teflon or a silicone based compound which will survive the temperatures of the molding operation. Additionally, the core pin can be covered with a high temperature sleeve, such as a polyimide or Teflon, as described hereinabove. Alternatively, or additionally, the core pin can be tapered, and in the two part core pin described hereabove, the distal core pin should be tapered with the large diameter at the distal end. This will provide for easier removal of the core pin with space for the lead wires, and will increase the stiffness of the proximal end of the distal lumen because the wall thickness will be greater.

A significant feature in the manufacturing process discussed hereabove is the prevention of the injected liquid plastic from passing into the inner lumen at the junction edge 124 where the lead wires emerge from the sidewall into the flared lumen section 76, as depicted in FIG. 4. It is to be appreciated that the shrink tube section 92 accomplishes this feature because the distal end 120 of the shrink tube section 92 shrinks around the lead wires to form a seal against the intrusion of injected liquid plastic into the flared lumen 76 during the molding process. Alternative configurations for accomplishing this feature are next discussed.

Figure 11:
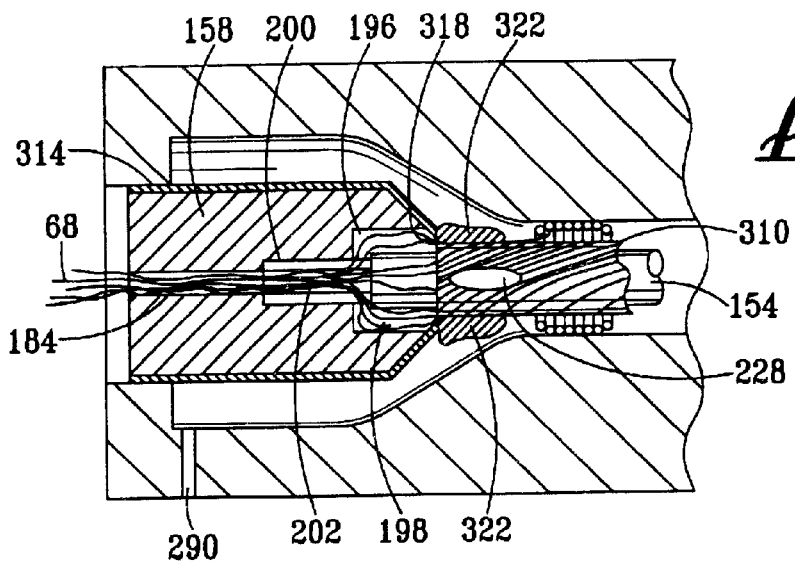
FIG. 11 is a side cross-sectional view depicting an alternative lead wire sealing step utilizable in the manufacturing of the device depicted in FIG. 2.

FIG. 11 is a side cross-sectional view of an alternative lead wire molding method. As depicted therein, a distal core pin 154 and a proximal core pin 158 are identical to those depicted in FIGS. 6–9, and spiral wound lead wires pass through the gaps 198 and 202 and the proximal bore section 184. The distal core pin 154 is surrounded by shrink tubing 310 and the proximal core pin 158 is also surrounded by shrink tubing 314, such that a gap 318 is formed between the shrink tubing sections 310 and 314 for the lead wires to pass therethrough and into the proximal pin bore 196. After the lead wires have been drawn through the proximal core pin 158, a quantity of potting compound 322 is placed into the gap 318 to seal it against intrusion by the liquid plastic in the injection molding process. Thereafter, the potting compound is cured and the core pin assembly is placed within the mold cavity, as previously described, and the injection molding process is next completed. The potting compound 322 acts to prevent intrusion of the liquid plastic into the flared lumen section 76 during the injection molding process in the same manner as the shrink tubing section 92, as discussed hereabove.

A variation on this lead wire molding method is to add another section of shrink tube (not shown) which covers the distal portion of shrink tube 314 and the potting compound 322. The added shrink tube section is then heated and shrunk, forcing the potting compound 322 into the interstices between the lead wires to provide a better seal. The potting compound is then cured. A further alternative variation is to extend the distal end of shrink tube section 314 beyond and over the potting compound 322. The extended portion of the shrink tube section 314 is then heated and shrunk, forcing the potting compound into the interstices between the lead wires to provide a better seal. The potting compound is then cured.

Figure 12:
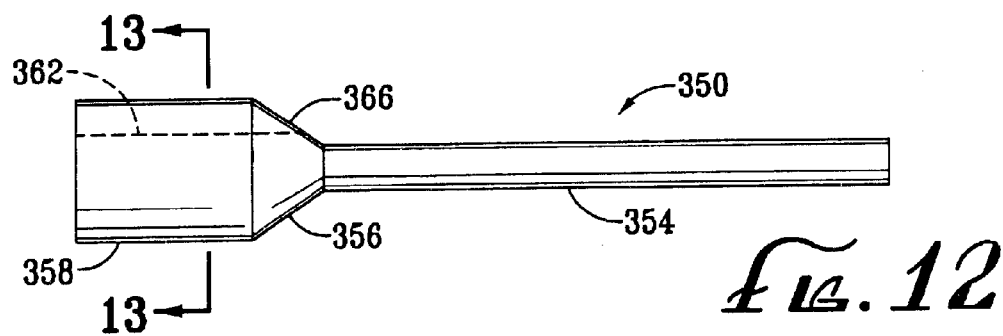
FIG. 12 is a side elevational view of an alternative unitary core pin, utilizable in the manufacturing of the device depicted in FIG. 2.
Figure 13:
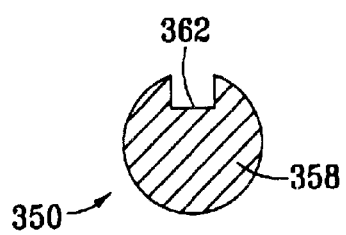
FIG. 13 is a cross-sectional view of the unitary core pin depicted in FIG. 12, taken along lines 13—13 of FIG. 12.

An alternative core pin design, comprising a single, solid core pin, is depicted in FIGS. 12 and 13, wherein FIG. 12 is a side elevational view and FIG. 13 is a cross-sectional view taken along lines 13—13 of FIG. 12. As depicted in FIGS. 12 and 13, the alternative core pin 350 includes a reduced diameter, cylindrical distal core pin section 354, a generally cylindrical flared core pin section 356 and a generally cylindrical proximal core pin section 358. A minimum of one longitudinal channel 362 is cut into the proximal core pin section 358, such that the distal end 366 of the channel 362 terminates in the flared section 356, to accommodate the passage of lead wires therethrough.

Figure 14:
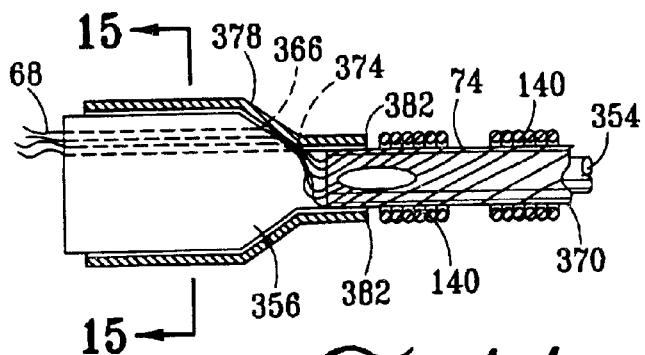
FIG. 14 is a side elevational view of the unitary core pin depicted in FIG. 12 having a plurality of coil-thermocouple assemblies disposed thereon for the manufacturing of the device depicted in FIG. 2.
Figure 15:
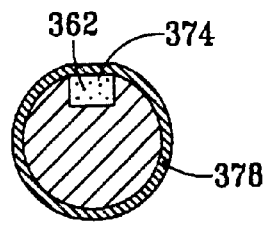
FIG. 15 is a cross-sectional view of the core pin assembly depicted in FIG. 14, taken along lines 15—15 of FIG. 14.

FIG. 14 is a side elevational view depicting the alternative core pin embodiment of FIGS. 12 and 13 having coil-thermocouple assemblies 140 disposed thereon, and FIG. 15 is a cross-sectional view taken along lines 15—15 of FIG. 14. As depicted in FIG. 14, a distal tubular section 370 is disposed upon the distal core pin section 354, and a plurality of coil-thermocouple assemblies 140, with spiral wound lead wires are disposed upon the tubular section 370. All of the lead wires 374 are passed through the channel 362, and a section of shrink tubing 378 is then placed over the proximal core pin section 358 to enclose the open distal end 366 of the channel 362. The shrink tubing 378 extends over the flared core pin section 356, such that the distal end 382 of the shrink tubing 378 fully seals the distal opening 366 of the channel 362. It is therefore to be appreciated that when the core pin 350 with assembled components (as depicted in FIG. 14) is placed in a mold cavity, and injection molding is undertaken, that liquid plastic in the injection molding process will be prevented from intrusion into the channel 362 by the shrink tubing section 378.

Figure 12A:
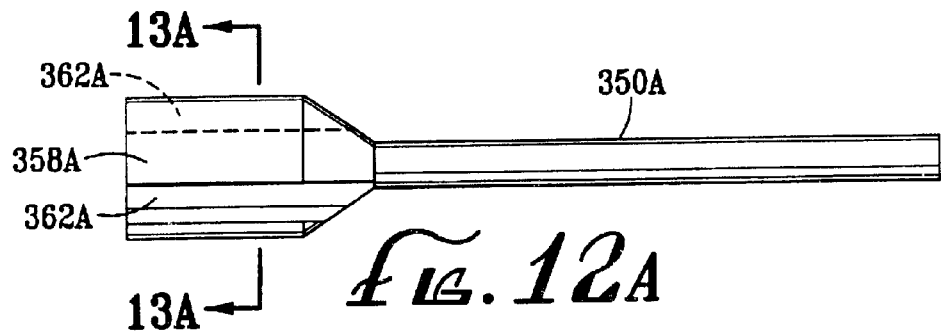
FIG. 12A is a side elevational view of another alternative unitary core pin, utilizable in the manufacturing of the device depicted in FIG. 2.
Figure 13A:
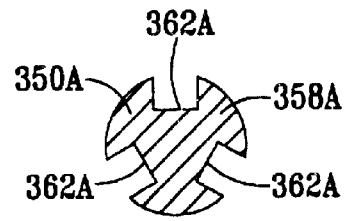
FIG. 13A is a cross-sectional view of the unitary core pin depicted in FIG. 12A, taken along lines 13A—13A of FIG. 12A.
Figure 14A:
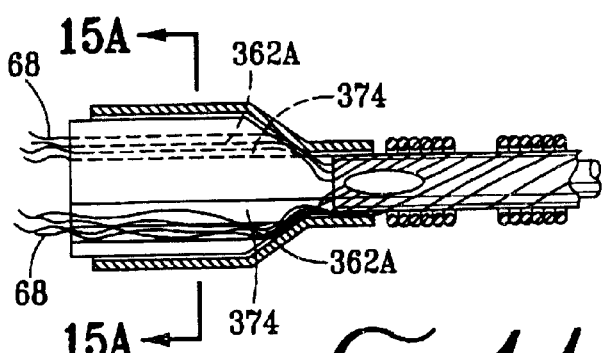
FIG. 14A is a side elevational view of the unitary core pin depicted in FIG. 12A having a plurality of coil-thermocouple assemblies disposed thereon for the manufacturing of the device depicted in FIG. 2.
Figure 15A:
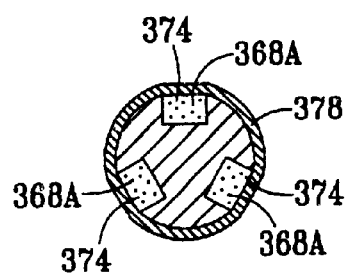
FIG. 15A is a cross-sectional view of the core pin assembly depicted in FIG. 14a taken along lines 15A—15A of FIG. 14A.

FIGS. 12A, 13A, 14A and 15A depict a single, solid core pin 350A that is similar to core pin 350 depicted in FIGS. 12—15; a significant difference between core pins 350A and 350 being that core pin 350A is formed with three longitudinal channels 362A cut into the proximal core pin section 358A. Therefore, as is best seen in FIGS. 12A and 13A, the proximal portion 358A of core pin 350A is formed with three longitudinal channels 362A that are disposed at approximately 120° arc spacing around the cylindrical proximal core pin portion 358A. As is best seen in FIGS. 14A and 15A, lead wires 374 from the electrodes and thermocouples are passed through the three channels 368A, and the three channels are enclosed by shrink tubing 378. The core pin embodiment 350A is advantageously utilized where a large number of lead wires must project rearwardly through the core pin channels.

It is to be recalled, as discussed hereabove, that the catheter distal end multi-electrode assembly 12 is designed for assembly on a catheter guide tube, wherein a steering mechanism is inserted through the central lumen 44, and that the end face 40 of the proximal wall 32 is bonded 22 to a guide tube distal end. The lead wires are passed through a guide tube lumen and the steering mechanism also passes through a guide tube lumen. In distinction thereto, the following description utilizes many of the novel features described hereabove to create a preferred embodiment that comprises a unitary, molded catheter having a multi-electrode distal end assembly.

Figure 16:
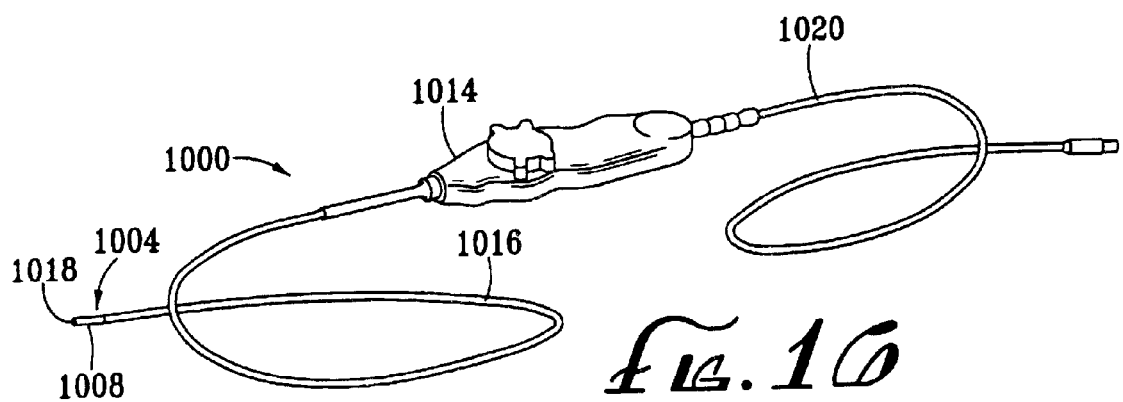
FIG. 16 is a perspective view of a catheter device having a unitary molded multi-electrode distal end of the present invention.

FIG. 16 is a perspective view of a catheter device, 1000 having a unitary, molded multi-electrode distal end assembly 1004. The device 1000 includes a handle 1014, a guide tube 1016, the multi-electrode assembly 1004, an electrode tip 1018, and an electrical interconnection cable 1020 that is engagable with a pin connector (not shown) that is disposed in the proximal end of the handle 1014. The catheter device 1000 performs essentially the same function as the catheter device 10 described hereabove. The difference between the devices 10 and 1000 being that the device 1000 is manufactured with the distal end assembly 1004 joined to the guide tube 1016 as a unitary device in a single molding step.

Figure 17:
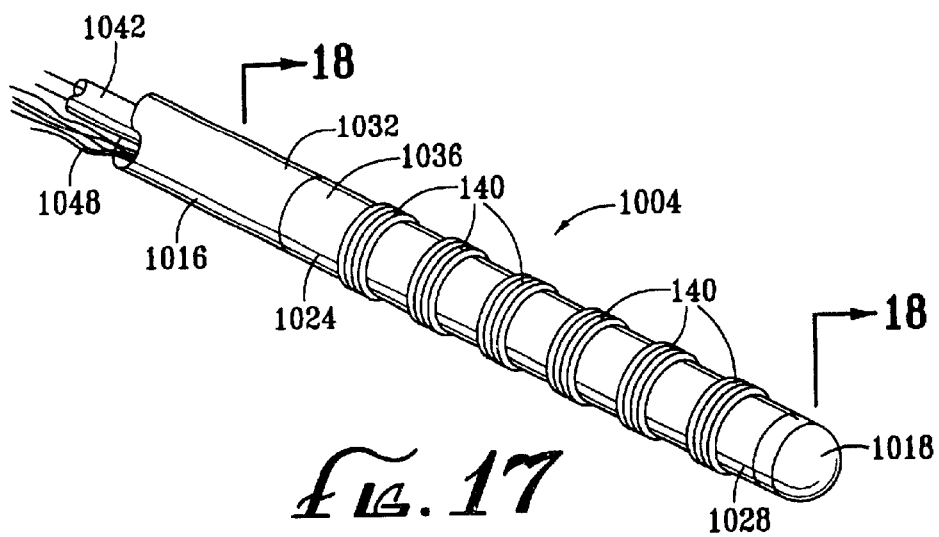
FIG. 17 is a perspective view of the unitary molded multi-electrode distal end of the catheter device depicted in FIG. 16.

FIG. 17 is a perspective view of the catheter end assembly 1004 of the catheter device 1000. As depicted therein, the catheter end assembly 1004 is a generally cylindrical member having a molded tubular wall 1024. A plurality of coil-thermocouple assemblies 140 (depicted and described hereabove with regard to FIG. 5) are molded into the wall 1024, and an electrode tip 1018 is molded into the distal end 1028 of the wall 1024. The distal end 1032 of the guide tube 1016 is molded into the proximal end 1036 of the sidewall 1024. A steering mechanism 1042 and lead wires 1048 from the coil-thermocouple assemblies 140 project through lumens formed in the guide tube 1016. The internal features of the catheter end assembly 1004 are next discussed with the aid of FIG. 18.

Figure 18:
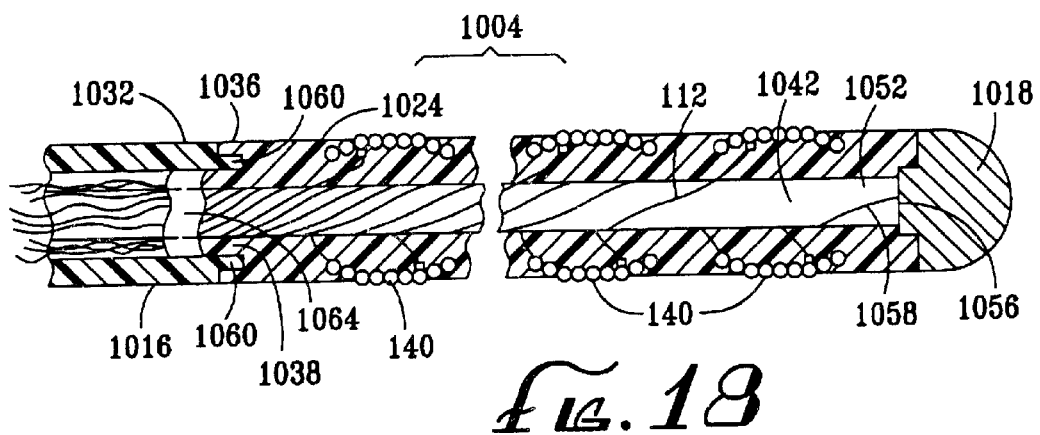
FIG. 18 is a cross-sectional view of a portion of the unitary molded multi-electrode catheter end depicted in FIG. 17, taken along lines 18—18 of FIG. 17.

FIG. 18 depicts a side cross-sectional view of the catheter end assembly 1004 depicted in FIG. 17. As depicted in FIG. 18, the catheter end assembly 1004 includes a centrally disposed steering mechanism 1042. The distal end 1052 of the steering mechanism is engaged to the proximal end 1056 of the electrode tip 1018 by adhesive bonding or soldering, and a tip lead wire 1058 is electrically connected to the tip 1018. The tip lead wire 1058, together with the lead wires from the coil-thermocouple assemblies are spiral wound 74 around the tubular steering mechanism 1042. At the proximal end 1036 of the sidewall 1024, the spiral wound lead wires are fed through a junction section 1038 into a lumen within the distal end 1032 of the guide tube 1016. The distal end 1032 of the guide tube 1016 may include a step 1060 or similar structure to aid in the molded joinder of the proximal end 1036 of the sidewall 1024 with the distal end 1032 of the guide tube 1016. A quantity of potting compound 1064 is disposed in the junction section 1038 of the guide tube 1016 with the molded sidewall 1024 to prevent injection molded material from passing rearwardly more than a predetermined distance into the lead wire and steering mechanism lumen within the guide tube 1016. The manufacturing steps for creating the device 1000 and particularly the catheter end assembly 1004, are next described with the aid of FIGS. 19–22.

Figure 19:
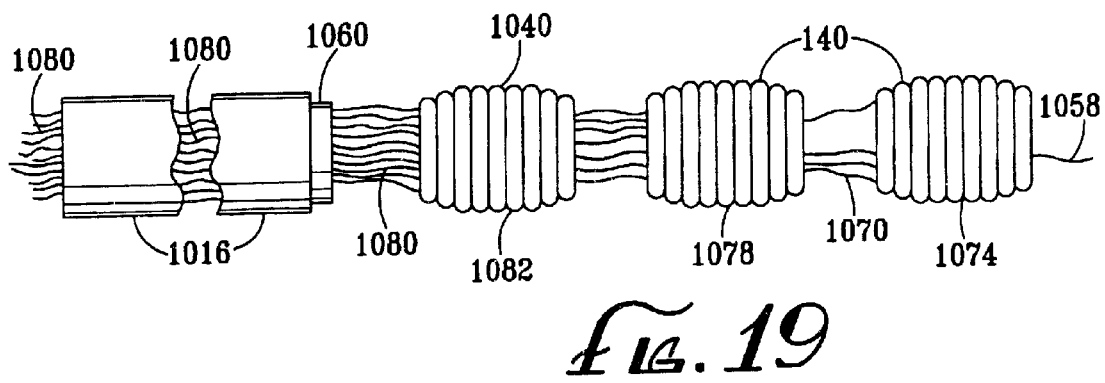
FIG. 19 depicts a first assembly step utilizing the coil-thermocouple assembly of FIG. 5 to manufacture the device depicted in FIGS. 16 and 17.

As depicted in FIG. 19, a plurality of coil-thermocouple assemblies 140 are first arranged such that the lead wires 1070 from the most distal coil-thermocouple assembly 1074 are passed through each of the successive, more proximate coil-thermocouple assemblies, such as 1078. When the assembly is completed, all of the coil-thermocouple lead wires 1080 pass through the most proximal coil-thermocouple assembly 1082. Additionally, the electrode tip lead wire 1058 is fed through all of the coil assemblies 140 to project forwardly from the most distal coil-thermocouple assembly 1074. All of the lead wires 1080 are then passed through a lumen in the guide tube 1016 to ultimately be electrically connected to a pin connector disposed in the handle 1014.

As depicted in FIG. 20, the steering mechanism 1042 is passed through a lumen in the guide tube 1016 and through the most proximally disposed coil-thermocouple assembly 1082. All of the lead wires 1080 are spirally wound 112 around the steering mechanism 1042 as the mechanism 1042 is maneuvered through the proximal coil assembly 1082. Thereafter, each of the successive coil-thermocouple assemblies are sequentially mounted upon the steering mechanism 1042 with the remaining lead wires being spirally wound around the steering mechanism 1042, until the most distal coil-thermocouple assembly 1074 is mounted upon the distal end 1052 of the steering mechanism. For ease of comprehension only the mounting of coil-thermocouple assembly 1082 is depicted in FIG. 20.

Thereafter, as depicted in FIG. 21, the electrode tip 1018 is bonded to the distal end 1052 of the steering mechanism 1042 and the tip electrode lead wire 1058 is electrically engaged to the tip electrode 1018. A quantity of potting compound may be inserted into the distal end of the steering mechanism to aid in blocking the flow of molding material into the steering mechanism. Lastly, a quantity of potting compound 1064 is pressed into the junction section 1038 at the distal end 1032 of the guide tube 1016 to prevent liquid molding material from traveling into the guide tube lumen during the upcoming injection molding process. The result of the manufacturing steps depicted in FIG. 21 is a catheter distal end assembly 1090 that is ready for injection molding as is depicted in FIG. 22.

FIG. 22 is a side cross-sectional view depicting the molding of the multi-electrode cathode end assembly 1004. As depicted therein, the assembly 1090 is disposed within a generally cylindrical mold cavity 1094 formed in a mold block 1098. The mold cavity sidewalls 1102 are dimensioned to contact the sidewall 1106 of the guide tube 1016 and the exterior surface 1110 of the electrode tip 1018. Additionally, and as was discussed hereabove with regard to the molding of the catheter tip embodiment 12, the mid-coil windings 138 of the coil-thermocouple assemblies 140 also contact the cavity sidewall 1102, whereas the tapered end windings 110 of the coil assemblies 140 do not contact the cavity sidewall 1102, such that the end windings 110 will become molded into the walls of the device. The mold block 1098 also includes an injection mold inlet port 1114 located at the distal end of the cavity 1094 and at least one outlet port 1118 located at the proximal end of the mold cavity 1094.

Having placed the assembly 1090 into the mold cavity 1094, molding material is injected into the inlet port 1114 to flow completely through the coil assemblies 140 and around the spiral wound lead wires and rearwardly to form the wall portions and outwardly through the outlet port 1118 as an indication that the mold cavity 1094 is completely filled. The molding material contacts and engages the electrode tip 1018 at the distal end of the mold cavity as well as the guide tube step 1060 at the distal end of the guide tube 1016. A preferred molding material is Pebax®. Thereafter, the appropriate mold curing steps are undertaken, following which the cured part is removed from the mold. The multi-electrode catheter end assembly 1004 is then completed, as depicted in FIG. 17 hereabove.

It is to be understood that the catheter end molding process described hereabove with regard to the creation of the multi-electrode catheter embodiments 10 and 1000 has a more generalized applicability. That is, the assembly and molding process can be utilized to manufacture many different types of catheter end assemblies that are utilizable in the minimally invasive surgery typified by the use of these catheter devices. Examples of such catheter end assemblies that can be manufactured utilizing the injection mold process described hereabove are next discussed.

Figure 23:
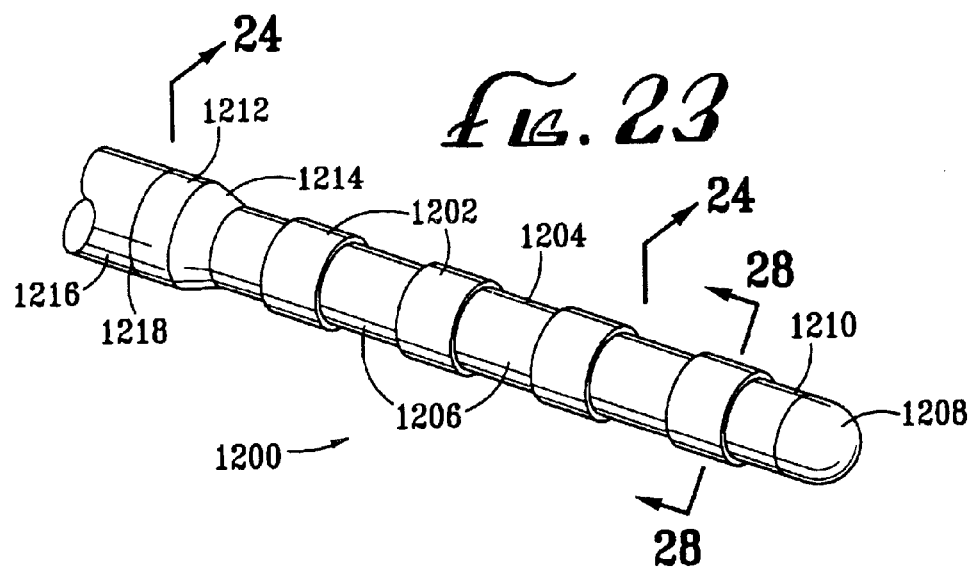
FIG. 23 is a perspective view of a catheter distal end assembly of the present invention including four ring electrodes.
Figure 24:
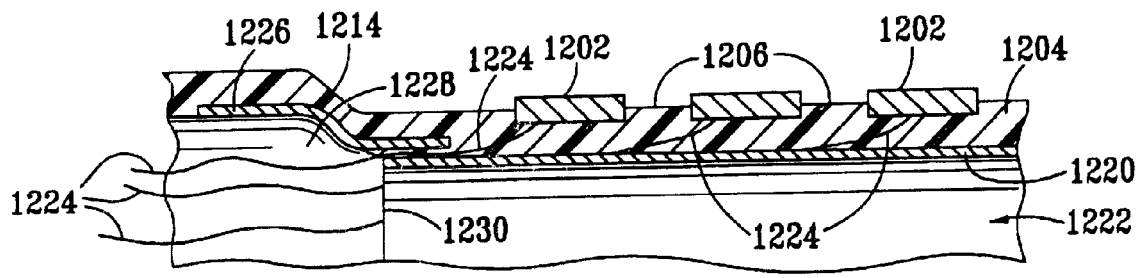
FIG. 24 is a cross-sectional view of a portion of the device depicted in FIG. 23, taken along lines 24—24 thereof.
Figure 27:
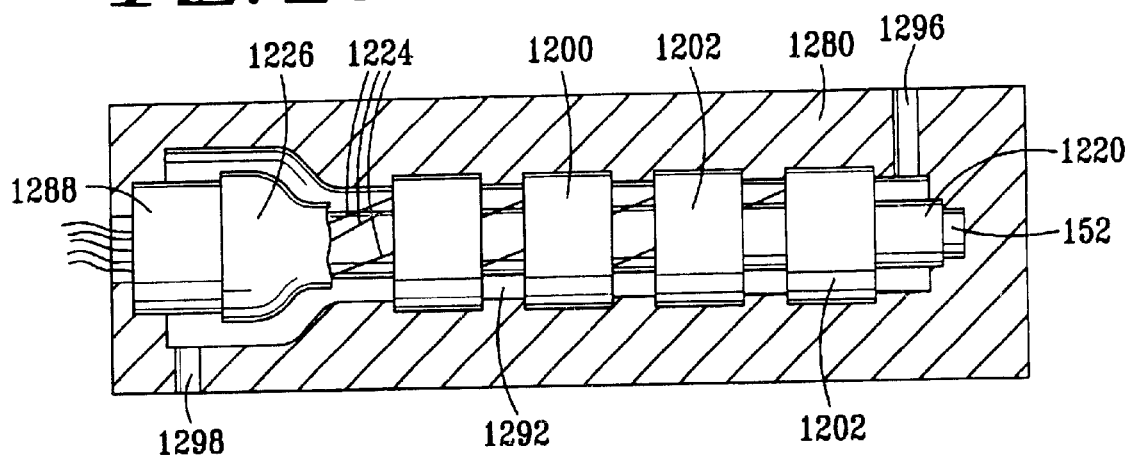
FIG. 27 depicts a four ring core pin assembly disposed within a mold for manufacturing.
Figure 28:
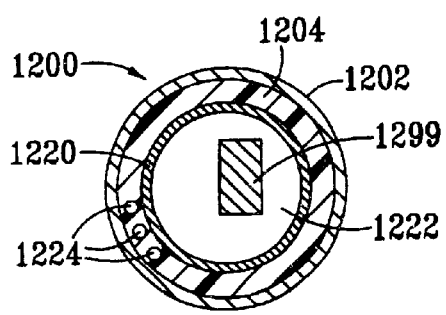
FIG. 28 is a cross-sectional view of the catheter distal end assembly depicted in FIG. 23, taken along lines 28—28 thereof.

FIGS. 23–28 depict a further molded catheter distal end assembly 1200 of the present invention, wherein FIG. 23 is a perspective view of the distal end assembly, FIG. 24 is a partial cross-sectional view of a portion of the wall of the device depicted in FIG. 23, FIGS. 25 and 26 depict core pin assembly steps, FIG. 27 depicts a molding step for the assembly 1200, and FIG. 28 is a cross-sectional view taken along lines 28—28 of FIG. 23. The catheter distal end assembly 1200 of FIG. 23 includes a plurality (four being shown) of ring electrodes 1202 that are molded into the distal cylindrical wall section 1204 of the device 1200, with gaps 1206 being formed between each electrode 1202. A distal end tip 1208 is engaged to the distal end 1210 of the wall 1204. An enlarged proximal wall section 1212 of the device 1200 is integrally formed with the distal wall section 1204 through a flared wall section 1214. The proximal end of the proximal wall section 1212 is engaged to the distal end of a guide tube 1216 at a joint 1218. A significant feature of the molded catheter end assembly 1200 is that the exterior surfaces of the ring electrodes 1202 extend radially outwardly beyond the surface of the cylindrical wall 1204, in order to make good contact with bodily tissue when the device 1200 is utilized in a diagnostic environment.

In FIG. 24 a cross-sectional view of a portion of the device 1200 is presented. In a manner similar to that depicted in FIG. 4, and described hereabove, a distal tubular member 1220 forms an interior lumen 1222 of the device 1200, and serves to form the interior wall surface of the distal wall portion 1204. A lead wire 1224 is engaged to each ring electrode 1202, and each lead wire 1224 is molded into the sidewall 1204 of the device 1200. A portion of shrink tube 1226 defines the inner surface of the flared section 1214, and the lead wires 1224 project from their molded-in disposition within the sidewall 1204 into the flared lumen portion 1228 at the junction 1230 of the tubular member 1220 with the shrink tube member 1226. As discussed hereabove, the external portions of the ring electrodes 1202 project radially outwardly relative to the outer surface of the distal wall section 1204.

FIG. 25 depicts a cathode distal end assembly 1240 having four ring electrodes 1202 disposed upon a section of distal tubing 1220 that is mounted upon a distal core pin 154. Each ring electrode 1202 is a thin walled cylindrical member, and an electrode lead wire 1242 is engaged to the inner surface of the electrode wall. A thermocouple 1244 is engaged to each ring electrode 1202 and a bifilar lead wire 1246 leads from each thermocouple 1244. Each lead wire 1242 and 1246 is spiral wrapped 1250 around the tubular member 1220, however, unlike the spiral wrapped lead wires 112, such as are depicted in FIG. 8, the lead wires 1242 and 1246 are counter spiral wrapped. That is, alternating ones of the lead wires 1242 and 1246 are spiral wrapped clockwise and counterclockwise. The counter spiral wrapping lowers the electrical noise within the device as compared to the spiral wrapped device as depicted in FIG. 8.

FIG. 26 depicts another electrode embodiment 1260, wherein four ring electrodes 1262 are disposed upon a distal tubular member 1220 that is mounted upon a distal core pin 154, in a similar manner to FIG. 25. A significant difference between the ring electrodes 1262 and 1202 of FIG. 25 is that the electrodes 1262 are formed with tapered proximal and distal edges 1264, as is depicted in FIG. 5A hereabove. As with the previously described tapered coil electrodes (such as electrode coil 50 depicted in FIGS. 3–5) the tapered edges 1264 are molded into the sidewall of a molded catheter assembly to control the effects of the generally higher electrical power density that occurs at the electrode edges, as discussed hereabove.

The stiffness of the various catheter end assemblies may be varied by altering the pitch of the spiral wrapped lead wires. Specifically, as depicted in FIG. 26, the spiral, wrapped lead wire 1266 from the distal electrode 1268 is initially wrapped with a generally coarse spiral pitch 1270 which gradually becomes a finer pitch as the lead wire 1266 traverses proximally through the remaining electrodes. At the proximal end 1230 of the tubular member 1220 the lead wires 1266 are spiral wound with a generally finer pitch 1272. The finer the spiral pitch of the wire, the stiffer the end assembly section becomes after molding.

In FIG. 27 the core pin and electrode assembly of the device 1200 is depicted within a mold block 1280; FIG. 27 is similar in many ways to the mold assembly depicted in FIGS. 10 and 11. As depicted in FIG. 27, the ring electrodes 1202 (four being shown for ease of depiction) are mounted around the cylindrical tubular member 1220 that is mounted upon the distal portion of a core pin 152. The lead wires 1224 are spiral wrapped around the tubular member 1220 and project through a proximal core pin section 1288. The shrink tube 1226 serves to prevent injection molded liquid plastic from penetrating into the proximal core pin 1288 as has been discussed hereabove. To create the radial extension of the outer surfaces of the ring electrodes relative to the distal wall section 1204, the interior wall 1292 of the mold block projects outwardly at the locations of the ring electrodes 1202 whereby, when liquid molding plastic is injected through the injection orifice 1296 to fill the mold and exit through the orifice 1298, the outer portions of the ring electrodes 1202 will extend beyond the outer surface of the sidewall portions 1204.

FIG. 28 is a cross-sectional view of the device depicted in FIG. 23, taken along lines 28—28 thereof, wherein the lead wires 1224 are shown disposed within the cylindrical wall 1204 that is surrounded by a ring electrode 1202. A generalized core component 1299 (shown as a rectangular body) is disposed within the central lumen 1222 defined by the tubular member 1220. It is to be understood that the generalized core member 1299, in various devices contemplated by the inventors as being within the disclosure of the present invention could be a steering mechanism as discussed hereabove, a section of straight or curved catheter stiffening member or other catheter components that, might be disposed within the central lumen of a catheter distal end assembly.

Figure 29:
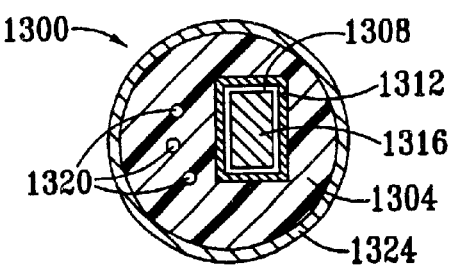
FIG. 29 is a cross-sectional view depicting an alternative embodiment to the embodiment depicted in FIG. 28.
Figure 30:
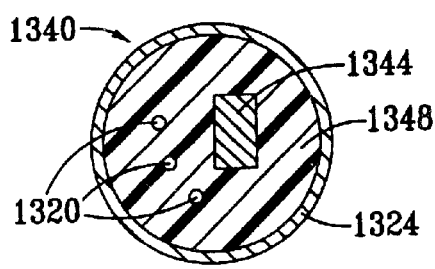
FIG. 30 is a cross-sectional view depicting another alternative embodiment to the embodiment depicted in FIG. 28.
Figure 31:
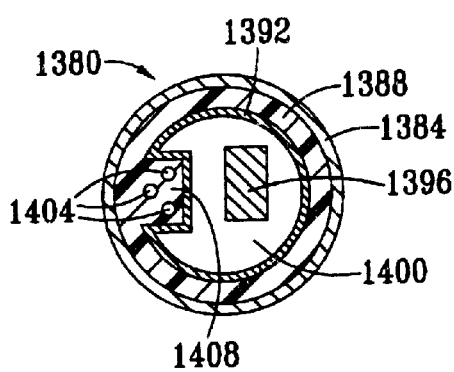
FIG. 31 is a cross-sectional view depicting a further alternative embodiment to the embodiment depicted in FIG. 28.

FIGS. 29, 30 and 31 are cross-sectional views, similar to FIG. 28, that depict further alternative embodiments of the present invention. In FIG. 29 an embodiment 1300 is depicted in which a substantially thickened sidewall 1304 is formed. A diminished central lumen 1308 is defined by a central tubular member 1312, and a generalized core component 1316 (similar to core component 1299) is disposed within the central lumen 1308. The lead wires 1320 that are engaged to the ring electrodes 1324 are disposed within the thickened wall section 1304.

FIG. 30 depicts a further alternative embodiment 1340 that is similar in many respects to embodiment 1300 depicted in FIG. 29. A significant difference between the embodiments 1340 and 1300 is that the generalized core component 1344 is molded into the wall section 1348. The lead wires 1352 of the electrodes 1356 are also molded into the wall 1348. A molding process to create the embodiment 1340 is similar to that depicted and described hereabove with regard to embodiment 1004, depicted in FIGS. 16–22. An example of a particular core component 1344 contemplated by the inventors is a nitinol spline member that is utilized in a basket electrode device as taught in U.S. Pat. No. 5,309,910 and discussed in detail herebelow.

Yet another alternative embodiment 1380 of the present invention is depicted in FIG. 31, wherein a ring electrode 1384 surrounds a wall portion 1388 defined by an interior tubular member 1392, and wherein a generalized core member 1396 resides within a central lumen 1400. In these respects, embodiment 1380 is similar to embodiment 1200 as depicted in FIG. 28. A significant difference between the embodiments depicted in FIGS. 31 and 28 is that the lead wires 1404 of embodiment 1380 are all molded within an inwardly projecting wall rib portion 1408. It will be understood by those skilled in the art, upon reading this disclosure, that a mold core pin having a longitudinal channel, and surrounded by shrink tube 1392, is utilized in the mold process to create the inwardly projecting wall rib 1408, and that the lead wires 1404 are all disposed within the core pin channel prior to the injection of liquid plastic into the channel in the molding process.

It is known by those skilled in the art that some catheter distal end assemblies are advantageously made with preformed curved contours, and such a curved end assembly 1500 is depicted in FIG. 32. FIG. 33 depicts a mold block for the creation of the pre-curved distal end assembly 1500 depicted in FIG. 32. The curved catheter distal end assembly 1500 includes a curved distal wall section 1504 which has a plurality of electrodes 1508 (three being shown for ease of depiction) molded therewithin, and a tip electrode 1512 engaged at the distal tip thereof. Electrode lead wires 1516 project proximally from the distal end assembly 1500 and the proximal end 1520 of the assembly 1500 is joined to the distal end of a guide tube 1524. As depicted in FIG. 33, a mold block 1550 is formed with a curved cavity 1554 that is defined by curved sidewalls 1558. The sidewall 1558 is formed with expanded electrode insertion sections 1562 and electrodes 1508 are shown disposed within the portions 1562. Lead wires 1516 from the electrodes 1508 project rearwardly through the mold cavity 1554 and through a lead wire slot 1570 formed in the wall of the mold 1550. A plug 1572, formed from a material such as potting compound, is utilized to plug the slot after the lead wires 1516 are drawn through the slot 1570. When liquid molding material is injected through the inlet orifice 1574 to fill the mold and exit through the exit orifice 1578, the electrodes 1508 and lead wires 1516 are molded into a solid, pre-curved catheter distal end wall section 1504. The tip 1512 is then engaged to the distal end of the molded assembly, and the proximal end 1520 of the molded assembly is then joined to the distal end of a guide tube 1524, as has been discussed hereabove.

FIGS. 34 through 37 depict a basket spline component that is within the scope of the present invention. As depicted in FIG. 34, the spline component 1600 includes a plurality of electrodes 1604 that are molded on a nitenol (or similar metal) spline core member 1608 having molded walls 1612. Lead wires 1616 from the electrodes 1604 project from an end 1620 of the molded walls 1612. As depicted in FIG. 35, the ring electrodes 1604 are mounted upon a central spline core member 1608, preferably having a rectangular cross section and being composed of a flexible material such as nitenol. The lead wires 1616 are successively disposed within each electrode 1604, as the several electrodes 1604 are mounted upon the spline core member 1608. When the electrode assembly is completed, all of the lead wires 1616 are disposed upon one side of the spline core member 1608, that side preferably being the concave side when the spline core 1608 is permitted to curve in its natural state as depicted in FIG. 34.

FIG. 36 depicts an electrode assembly 1620 disposed within a mold 1640. The end portions 1644 of the spline core member 1608 are held within end portions of the mold cavity 1648, such that the spline core member 1608 is held straight, rather than curved. In an alternative mold embodiment, similar to the mold depicted in FIG. 33, the mold cavity 1608 could be curved to hold the spline core member 1608 in its natural curved state. The mold cavity 1648 is preferably formed with electrode ring holding sidewall projections, such as sidewall projections 1562 of mold 1550 depicted in FIG. 33. A lead wire slot 1652 is formed through the mold 1640 such that the electrode lead wires 1616 project out of the mold. It is therefore to be appreciated that when liquid injection molding material is injected through the inlet orifice 1660 that it will pass through the mold cavity 1648 to the exit orifice 1664 to form the walls 1612 of the spline assembly 1600 depicted in FIG. 34.

FIG. 37 is a cross-sectional view of the spline embodiment 1600 taken along lines 37—37 of FIG. 34. As depicted in FIG. 37, the rectangular spline core member 1608 is molded into the wall 1612 which also holds the ring electrodes 1604. The lead wires 1616 (six being shown) are all disposed on the concave side of the spline core member 1608.

An alternative embodiment 1700 of the spline 1600 is depicted in FIG. 38, which shows a ring electrode 1604 engaged within a molded wall section 1612, and wherein the lead wires 1616 are also molded into the wall section 1612. The significant difference between the spline embodiment 1700 of FIG. 38 and the spline 1600 of FIG. 37 is that the spline core member is not molded into the device. Rather, a core pin is utilized to form a central lumen 1708 in a molding process similar to that discussed hereabove with regard to distal assembly 12. Following the molding process which creates the lumen 1708, the rectangular spline core member 1608 is inserted within the lumen 1708.

The spline assembly 1600 is designed for significant flexing during its usage. This flexing creates the possibility that one or more lead wires may be pulled away from the electrical attachment of the lead wire with its designated electrode. FIG. 39 depicts an alternative spline embodiment 1750 that is similar in many respects to spline embodiment 1600, particularly as depicted in FIG. 35. The significant difference between embodiments 1750 and 1600 is that the electrode lead wires 1754 of spline embodiment 1750 are not straight; rather they are formed with a plurality of bends 1758, in what might be called an accordion manner. It is therefore to be appreciated that when the accordion shaped lead wires 1754 are molded into the walls of a spline assembly that the lead wires 1754 are able to withstand greater flexing without separation from their associated electrodes.

The molding method of the present invention is utilizable for many types of catheter distal end assemblies, including optical and ultrasonic imaging catheter distal end assemblies. FIG. 40 generally depicts an imaging distal end assembly 1800 having an imaging distal tip 1804 which may hold an optical or ultrasonic imaging device, and a body portion 1808 that is molded in accordance with the present invention. Electrical lead wires 1812 are molded into the sidewall of the body portion 1808 and a central lumen 1816 may be formed therein for the insertion of a steering assembly, as has been discussed hereinabove.

FIG. 41 depicts a mold block 1820 for manufacturing the imaging catheter distal end assembly 1800. As depicted in FIG. 41, the mold block 1820 includes a generally cylindrical mold cavity 1828 formed therein. The mold cavity 1828 includes a distal end portion 1832 for the receipt of a distal tip imaging device 1804 therewithin. A generally cylindrical core pin 1842 is centrally disposed within the cavity 1828 and electrical lead wires 1812 (if the imaging device 1804 requires them) are preferably spirally wound around the core pin 1842, such that the wires 1812 will become molded into the sidewall of the device when the mold cavity 1828 is filled. It is therefore to be understood that when liquid injection molding material is injected through the mold inlet orifice 1850, through the mold cavity 1828 and to the mold exit orifice 1854, that upon curing, the liquid plastic material will form the walls 1828 of the molded optical or ultrasonic imaging catheter distal end assembly. Thereafter, a steering device and an ultrasonic or optical imaging device with attached optical fibers for an optical imaging device may be inserted within the core pin bore. Alternatively, a steering device and/or optical fibers can be installed within the mold cavity before injection of the liquid material, as is taught above with the aid of FIG. 22. Optical and ultrasonic imaging devices as are discussed hereabove are taught in detail in copending U.S. patent application Ser. No. 08/1738, 822, filed Oct. 28, 1996, the contents of which are incorporated herein as though set forth full.

It is understood that those skilled in the art will conceive of various alterations and modifications of the present inventions upon reading the preceding detailed description, and/or utilizing the devices described herein. It is therefore intended by the inventors that the following claims cover all such alterations and modifications that include the true spirit and scope of the inventions described herein.

What We claim is:

1. A catheter distal end assembly, comprising:
   a molded body portion having a central lumin therein; and
   a tapered coil or smoothly tapered ring electrode having at least one electrical lead wire engaged thereto, said electrode and lead wire being molded into said molded body portion, said lead wire being molded along said central lumen.

2. The catheter distal end assembly of claim 1, wherein the lead wire is spiral wrapped along said central lumen.

3. The catheter distal end assembly of claim 1, further comprising a temperature sensor located proximate to the electrode, the sensor having a sensor lead wire attached thereto, wherein the sensor is engaged to a portion of the electrode that is exposed on an outer surface of the molded body portion of the catheter distal end assembly.

4. The catheter distal assembly of claim 3, wherein the electrode lead wire is spiral wrapped in a clockwise direction along the central lumen and the sensor lead wire is spiral wrapped in a counterclockwise direction along the central lumen.

5. The catheter distal assembly of claim 3, wherein the electrode lead wire is spiral wrapped in a counterclockwise direction along the central lumen and the sensor lead wire is spiral wrapped in a clockwise direction along the central lumen.

6. A catheter, comprising:
   a handle;
   a guide tube having a proximal end and a distal end, said guide tube proximal end being engaged with the handle; and
   an end assembly disposed at the guide tube distal end, said end assembly including a molded body portion and at least one component means selected from the group consisting of a coil electrode or an imaging device, said component means having at least one electrical lead wire engaged thereto, wherein said component means and said lead wire are molded into said molded body portion, said lead wire being molded in a spiral manner within said molded body portion.

7. The catheter of claim 6, wherein the lead wire passes from the molded body portion to the guide tube, the lead wire becoming freely disposed within the guide tube.

8. A catheter distal end assembly, comprising:

a molded body portion; and a coil or smoothly tapered ring electrode having tapered proximal and distal end portions and at least one electrical lead wire engaged thereto, said electrode and lead wire being molded into the molded body portion such that said tapered proximal and distal portions are at least partially molded into said molded body portion.

9. The catheter distal end assembly of claim 8, wherein the coil electrode comprises a plurality of coil windings, including end coil windings and middle coil windings.

10. The catheter distal end assembly of claim 9, wherein the end coil windings are decreased in diameter relative to the middle coil windings.

11. The catheter distal end assembly of claim 9, wherein the middle coil windings are exposed on an outer surface of the molded body portion of the catheter distal end assembly and wherein the end coil windings are disposed within the molded body portion of the catheter distal end assembly.

12. The catheter distal end assembly of claim 8, wherein the molded body portion includes a central lumen, said electrode lead wire being spirally wound around the central lumen with a varied pitch, wherein the pitch is a coarse spiral pitch at a distal end of the molded body portion and becomes a finer spiral pitch as the electrode lead wire traverses proximally through the central lumen of the molded body portion.

13. The catheter distal end assembly of claim 8, wherein the electrode lead wires are molded within an inwardly projected rib portion located on the molded body portion.

14. The catheter distal assembly of claim 8, wherein the molded body portion has a distal end portion and a proximal end portion, said distal end portion being reduced in diameter relative to the proximal end portion.

15. A catheter distal end assembly, comprising:

a molded body portion, a flexible spline core member located within the molded body portion, a tapered coil or smoothly tapered ring electrode surrounding the spline core member, and an electrode lead wire molded within the molded body portion alongside the spline core member and formed with a plurality of bends.

16. The catheter distal end assembly of claim 15, wherein the spline core member is molded within a molded wall of the molded body portion.

17. The catheter distal end assembly of claim 15, wherein the spline core member is freely located within a central lumen of the molded body portion.

18. A catheter, comprising:

a handle;

a guide tube having a proximal end and a distal end, said guide tube proximal end being engaged with the handle; and an end assembly disposed at the guide tube distal end, said end assembly including a molded body portion and a tapered coil electrode means for ablating tissue, said electrode means having at least one electrical lead wire engaged thereto, wherein said electrode means and said lead wire are molded into said molded body portion, said lead wire being molded in a spiral manner within said molded body portion.

* * * * *